US006579706B2

United States Patent
(12) United States Patent
Grae

(10) Patent No.: US 6,579,706 B2
(45) Date of Patent: *Jun. 17, 2003

(54) RAPID THERMAL CYCLE PROCESSING METHODS AND APPARATUS

(75) Inventor: Joel B. Grae, Peekskill, NY (US)

(73) Assignee: IB2, LLC, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/931,827

(22) Filed: Aug. 17, 2001

(65) Prior Publication Data

US 2002/0168734 A1 Nov. 14, 2002

Related U.S. Application Data

(63) Continuation of application No. 09/508,889, filed as application No. PCT/US98/19815 on Sep. 23, 1998, now Pat. No. 6,277,610

(60) Provisional application No. 60/060,690, filed on Sep. 23, 1997.

(51) Int. Cl.[7] .......... C12N 13/00
(52) U.S. Cl. .......... 435/173.5
(58) Field of Search .......... 435/173.5

(56) References Cited

U.S. PATENT DOCUMENTS

| | | | | |
|---|---|---|---|---|
| 4,975,246 A | * 12/1990 | Charm | | 422/21 |
| 5,389,335 A | * 2/1995 | Charm et al. | | 422/21 |
| 6,277,610 B1 | * 8/2001 | Grae | | 435/173.5 |

FOREIGN PATENT DOCUMENTS

| | | | |
|---|---|---|---|
| RU | 2052967 | * 3/1993 | |
| WO | WO 9732483 A1 | * 9/1997 | A23C/3/02 |

* cited by examiner

*Primary Examiner*—Jon P. Weber
(74) *Attorney, Agent, or Firm*—Milde & Hoffberg LLP

(57) ABSTRACT

A system and method for processing a cells, the method comprising the steps of providing the cells to be processed in a liquid medium; and heating the liquid medium containing the cells at a rate and through a range sufficient to cause an instability in at least one of the cellular membranes. The method may be used to fuse the structure with another membranes, or to reduce the integrity of the membranes. The system atomizes a medium containing the cells into small droplets and subjects them to an environment containing steam vapor while moving at high velocity, to rapidly increase the droplet temperature to the steam temperature by release of the latent heat of vaporization.

20 Claims, 16 Drawing Sheets

Phospholipid Phases

Corresponding $^{31}$P-NMR Spectra

Bilayer

Hexagonal (H$^{11}$)

Phases in which
isotropic motion occurs:

1. Vesicles
2. Inverted micellar
3. Micellar
4. Cubic
5. Rhombic

|—40 ppm—|   H →

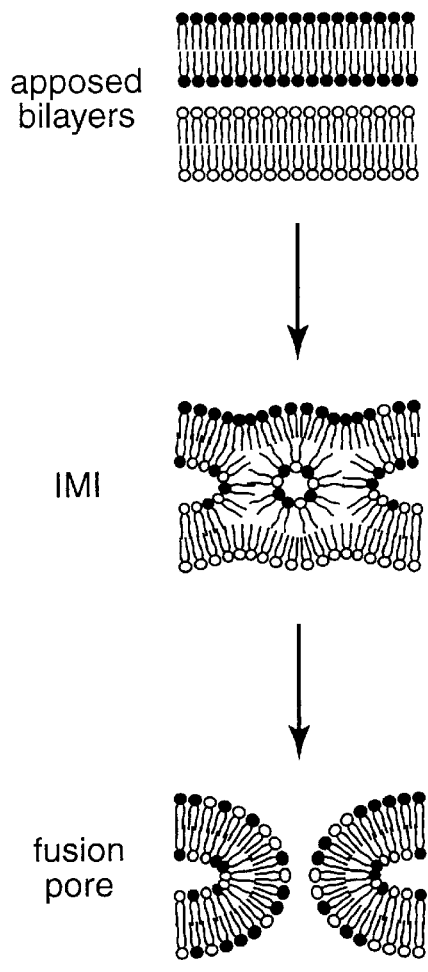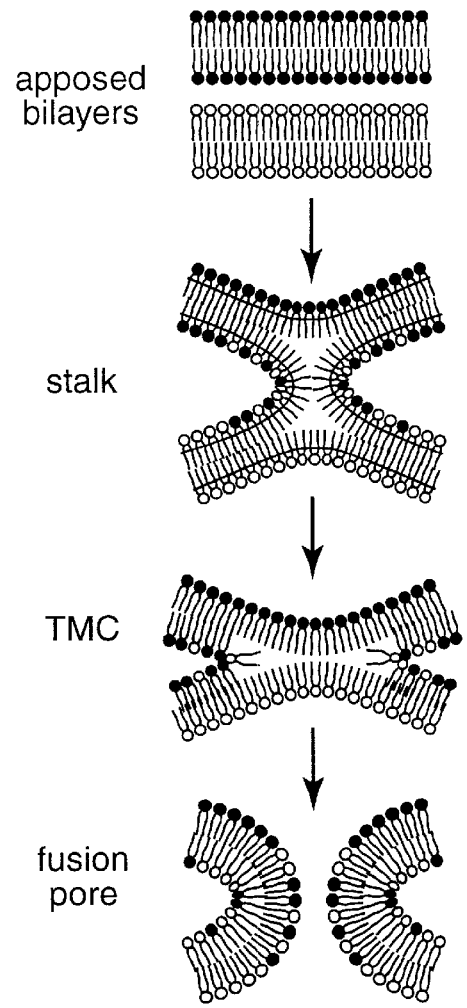
Fig. 17 A
Fig. 17 B

RAPID THERMAL CYCLE PROCESSING METHODS AND APPARATUS

The present application is a continuation of U.S. patent application Ser. No. 09/508,889 filed Mar. 17, 2000, now U.S. Pat. No. 6,277,610 issued Aug. 21, 2001 which is a 371 application of PCT/US98/19815, filed Sep. 23, 1998, which claims benefit from U.S. Provisional Patent Application No. 60/060,690, filed Sep. 23, 1997.

FIELD OF THE INVENTION

The present invention relates to the field of thermal processing of biological matter to alter or kill the cells. More particularly, a rapid rise in temperature is employed in a manner which avoids denaturation of proteins while altering membrane properties.

BACKGROUND OF THE INVENTION

It is well known that biological cells may be killed in a manner of Pasteurization, in which the time temperature product of a process is sufficient to denature cell proteins necessary for vitality. Other cell killing mechanisms are known which involve physical process, such as shear forces, ultrasonic cavitation, alteration in membrane properties through the insertion of pores, and the like.

A number of methods are known for reducing bacterial activity in liquids. Traditionally, a so-called "Pasteurization" process is employed, which operates by the principles of thermal denaturation of proteins to inactivate bacteria. Thus, the liquid is raised to a particular temperature for a proscribed duration, to effect a statistical reduction in the number of, or even elimination of all viable bacteria. In an effort to reduce a duration of the process, high temperatures may be employed, which raise the temperature of the fluid to, e.g., 150° C. for 2–4 seconds under pressure, followed by a flashing (rapid boiling) to lower the temperature, thus limiting the duration of the treatment. Such systems thus require a very high temperature, and may alter a taste of a potable liquid or food product, such as is the case with milk. Depending on how the heat is applied, precipitation of proteins in the product or other physical changes may occur. In addition, the presence of oxygen during treatment may cause accelerated oxidation.

The heat treatment processes for fluid food products (e.g., milk) are applied for destroying disease-causing microorganisms, as well as inactivating microorganisms which may spoil the food. In many known processes, the bacterial reduction is a preservation technique which extends the shelf life, but sterilization is not achieved. Some of these pasteurization techniques involving heat treatment of food products, for instance, milk, are disclosed in USSR Pat. No. N 463,250 M KI A 23c 3/02 and N 427532 M KI 28 9/00 A 23c 3/02.

The most widely used Pasteurized technique involves subjecting food products to heat treatment as high as 65–75° C. and exposing same to this temperature for a period of time of 30 minutes. This is the so-called long-term heat treatment. The second technique involves subjecting food products to heat treatment at a temperature of 70–75° C. and exposing same to this temperature for a period of time of 2–4 minutes. The third technique involves subject food products to short term heat treatment at a temperature of 95° C. and exposing same to this temperature for 30 seconds. The fourth technique includes ultra high temperature heat treatment. It involves subjecting food products to a temperature of 110–140° C. and exposing same to this temperature for a period of time of 2–3 seconds. These treatment are thus based on a thermostability time-temperature relationship of microorganisms. Thermostable life-time is defined as a life-time of microorganisms at a given temperature. The higher the temperature, the shorter the thermostable period. An effective Pasteurization treatment thus subjects food products to heat treatment at a certain temperature for a period of time which is longer than the thermostable period.

These prior art techniques are generally directed toward the thermal denaturation of essential cell elements, they effectively cook the treated medium, including any biological organisms therewithin. Thus, proteins lose their tertiary structure, cells are killed, and heat labile components are adversely affected. Sediments may also be formed, which may necessitate regular cleaning of the system, especially any higher temperature portions, such as heat exchange surfaces.

Some of these drawbacks can be avoided by using the direct heat treatment, which heats the product by way of direct contact of the product subjected to Pasteurization with the heating medium, for instance, steam, rather than through a heat transferring surface of heat exchange equipment. This method eliminates release of the milk "stone" in the heating zone and lessens its appearance on other surfaces of the equipment. These known methods transfer the product into the Pasteurizer, and inject steam made from potable water to a desired temperature, for a desired period. The product is cooled and excess water from condensed steam eliminated. This technique allows a relatively quick heat treatment of the product, and has been found of particular use in ultra high temperature heat treatments. The technique avoids exposure to temperatures higher than a desired final temperature, and thus may limit sedimentation, which may appear, for example, as milk "stone" in a Pasteurization process. Where direct steam contact is used, it dilutes the medium, for example up to 30% of the product mass, with an ultrahigh temperature Pasteurization technique, which subsequently is often removed.

These known methods of Pasteurization strive to maintain laminar flow of milk during the process, and thus do not atomize the milk. As a result, these systems fail to raise the temperature of the bulk of the milk at a rapid rate, and rather gradually raise the bulk temperature to the Pasteurization temperature, at which the milk is maintained for the desired period. Of course, a small surface layer may experience rapid temperature rises.

Zhang, et al., "Engineering Aspects of Pulsed Electric Field Pasteurization", Elsevier Publishing Co. (1994) 0260-8774(94)00030-1, pp. 261–281, incorporated herein by reference, relates to Pulsed Electric Field Pasteurization, a non-thermal Pasteurization method. This method (as well as other biological treatment methods) may be combined with other methods, to enhance efficacy of the composite process, while avoiding the limitations of an excess exposure to any one process.

RU 2,052,967 (C1) relates to a rapid temperature rise bactericidal treatment method, similar to the present method, but intended to non-selectively kill organisms. Abrams et al, U.S. Pat. No. 3,041,958 relates to a steam processing temperature control apparatus. Wakeman, U.S. Pat. No. 3,156,176 relates to a steam Pasteurization system. Stewart, U.S. Pat. No. 3,182,975 relates to a steam injection heater, which employs impeller blades to mix steam and milk for rapid heating. Engel, U.S. Pat. No. 3,450,022 relates to a steam infuser for high temperature steam treatment of liquids. Nelson, U.S. Pat. No. 3,451,327 relates to a steam injector for a milk sterlizer. This device is intended to bring the milk to a high temperature, and thus allows thermal communication between the steam and milk prior to venting. De Stoutz, U.S. Pat. No. 3,934,042 relates to a system for treating beverages, including milk, beer, wine and fruit juices, for sterilization or Pasteurization. The liquid is held at elevated temperatures for extended periods. Janivtchik, U.S. Pat. No. 4,160,002 relates to steam injectors for Pasteurizing milk using pressurized steam. Wakeman, U.S. Pat. No. 4,161,909 relates to an ultrahigh temperature heating system for heating, e.g., milk. The milk falls in a curtain configuration in a steam chamber. The milk held at a high temperature after heating. Nahra et al. U.S. Pat. No. 4,591,463, and Nahra et al. Re. 32,695, incorporated herein by reference, relate to a milk ultra Pasteurization apparatus in which sheets of milk fall within a steam filled chamber for ultra high temperature Pasteurization. Bronnert, U.S. Pat. Nos. 4,787,304 and 4,776,268 relate to an infusion heating apparatus for sterilizing liquid food products, having a porous steam dispensing cylinder or diffuser located along a central axis of a treatment vessel. Sanchez Rodriguez, U.S. Pat. No. 5,209,157 relates to a diary preparation system which involves an ultrahigh temperature treatment step.

It is also well known to fuse cell membranes through the use of so-called fusion proteins, chemical agents, photonic effects, and possibly by application of heat. Cell fusion has been used to form hybrid cells or hybridomas, to insert cell surface proteins or to alter cell cytoplasmic chemistry.

The Rapid Thermal Cycle Processing (RTCP) Technology is relatively unexplored as a mechanism for treating of cells. It is known, however, that RTCP is capable of killing bacteria at temperatures below those which tend to denature bacteria.

The RTCP process, also known as MilliSecond Pasteurization ("MSP") involves the heating of fluid droplets with saturated steam, at a high rate of increase, for example, over a thousand degrees per second, to a desired temperature, typically under conditions which do not denature (a chemical process which alters structure) proteins. When appropriately processed, fluids may be sterilized, without otherwise changing macromolecular structures.

RTCP technology has been proposed for the "Pasteurization" of milk, to kill bacteria and spores in the milk.

A microwave Pasteurization and Sterilization process is disclosed in Stanley E. Charm et al. (Charm Sciences, Inc., Malden Mass.), U.S. Pat. Nos. 4,839,142, 4,975,246, and 5,389,335, expressly incorporated herein by reference. These patents disclose a process which is said to sterilize food products without substantial protein denaturation by rapid heating (25–8000° C. per second) and cooling of the treated product within a short time.

SUMMARY OF THE INVENTION

The present invention provides a rapid thermal cycle processing system which provides a high rate of temperature change, which primarily is directed to formed cell components, such as membranes. In particular, the outer cell membrane is a focus of the action.

While the mechanism of action is subject to speculation, it is believed that a primary effect of the rapid temperature transition is to generate a shock wave. In addition, the rapid rate of temperature rise is fast enough that diffusion of lipids in the membrane is incomplete, so that domains of membrane remain with differing characteristics, such as glass transition temperature. Thus, the temperature rise may have a different qualitative effect on certain regions as compared to others.

While RTCP is capable of killing cells, likely by disrupting membranes, the RTCP process, need not always be applied under such conditions as kill the cells. This readily apparent from studies which were performed in which a surviving fraction of bacteria remained. In some tests, these bacteria formed aberrant colonies when cultured. Thus, by subjecting the cells to RTCP under mild conditions, alterations may occur which are non-lethal.

This observation has presented many significant and exciting opportunities. These opportunities include cell membrane fusion, presentation of cellular antigens for immune response, induction of specific cell responses, and cellular "reprogramming". RTCP also has potential industrial applications in the biotechnology industry for sterilization, cell lysis, cell manipulation and cell fusion, and in the chemical industry for rapid and uniform heating, selective melting, reaction initiation and encapsulation or trapping of particulates.

The present invention seeks to alter cell characteristics by a thermal shock process, which may be used, for example, to inactivate or kill bacteria, alter cell surface chemistry or antigenicity, disrupt membranes, activate cell functions or responses, disaggregate cells, as a pretreatment before cell fusion or infection, activate or change the function of a cellular parasite (bacteria, mycoplasma, virus, prion, etc.), affect mitochondrial functioning or the functioning of other organelles. On an organism level, the present invention may be used to treat bacterial infections, such as osteomyelitis, vital infections such as AIDS, human or animal Herpes viruses (including HHV-5 and EBV, as well as CMV, HSV-1, HSV-2, VZV, HHV-8, and the like), treat cancer, sarcoma, mesothelioma, teratoma or other malignancy or neoplasm, treat skin conditions, such as psoriasis, treat inflammation, treat fungal diseases, blood borne diseases, leukemias and the like. The present invention may also have utility in the treatment of syndromes, which may be multifactorial in origin and involve an immunological component or defect. Therefore, the present invention may also find utility in the treatment of chronic fatigue syndrome (CFS), for example by applying immune stimulation therapy through treatment of blood or blood components.

The broad utility of the present invention comes from its ability to carefully control a stress applied to a cell. This stress may, of course, kill the cell or selectively kill a subpopulation of cells, but more importantly, it is believed that the present invention may be applied to cells to have a measurable non-transient effect which does not immediately result in cell death. In this manner, the present method provides a new manipulation modality for cells.

In contrast to known cellular thermal inactivation methods, the major aspects of the present invention do-not rely on thermal denaturation of cellular proteins and enzymes, but rather on a rapid temperature rise which irreversibly changes the cell, at temperatures and energy levels below those required by traditional Pasteurization processes.

In particular, according to one embodiment of the system and method according to the present invention, a product is treated such that the temperature of a medium in which all or a portion of the cells exist rises at such a rapid rate that normal accommodation mechanisms, which might allow the cell to avoid permanent effect from a slower temperature rise rate treatment, are unavailable or ineffective. Thus, it is an aspect of the present invention to alter cell functioning based on a rate of temperature change during treatment, rather than based on a time-temperature product function or a maximum temperature.

The present invention is thus believed to operate by a physical principle different than thermal denaturation, the principle behind Pasteurization. Rather than a thermal denaturation of the proteins, as well as proteins which may be in the extracellular medium, one aspect of the present invention operates by thermal shock, which is believed to disrupt or alter membrane structures or membrane components of cells. Typical media for treatment include milk, egg white, blood plasma, cell culture medium, fermentation broth, fruit juices, and the like.

Thus, rather than a high temperature, per se, the present invention requires a high rate of temperature rise. The resulting maximum temperature may be limited to temperatures which do not denature various proteins, e.g., a maximum temperature of 0–75° C. It is clear, therefore, that the maximum temperature may remain sub-physiological, or rise to relatively high levels. For food processing, the maximum temperatures will often be on the higher end of the scale, in the 40–75° C. range, while in medical or pharmaceutical process, the maximum temperatures will often be in the middle of the range, e.g., 15–55° C. Sterilization of non-heat labile media may occur at high temperatures, e.g., greater than 110° C., for example where the media is contaminated by thermotrophic organisms.

One theory of operation of the present invention relates to the glass transition temperature of membrane structures. Cellular membranes are generally formed of phospholipid bilayers with proteins, lipoproteins and glycoproteins inserted on the inside, outside, or protruding through the membrane. The membrane, especially the fatty acid chains of the phospholipids, are physiologically maintained in a fluid condition, and thus lipids and proteins are motile across the surface of the membrane. For example, under comparable circumstances, a lipid molecule may travel at a rate of about 2 microns per second, with proteins traveling at a rate of several microns per minute, in the plane of the membrane. Membrane components, though mobile in the plane of the membrane, are generally slow to switch or invert between the outer and inner surface. For example, transverse diffusion rate of phospholipids is about $10^{-9}$ the rate of lateral diffusion, for a typical 50 Å distance (the thickness of a phospholipid bilayer membrane). The viscosity of a cell membrane typically is about 100 times that of water.

On the other hand, the membrane structures of living cells have some long-term ordering of molecules, especially the structures on the surface of the membrane (as opposed to the lipid phase in the middle of the membrane), and therefore are in this sense somewhat crystalline. Thus, the phrase "liquid crystal" is apt for the composite structure. Among other functions, the controlled membrane fluidity is believed to be necessary for various mediated transport systems which involve the movement of carriers within or through the membrane. The membrane proteins also have, in their natural state, a separation of charged and uncharged portions, allowing stable insertion of lipophilic portions of the proteins into the membrane structure, with hydrophilic portions protruding extracellularly or intracellularly from the membrane, into the cytoplasm or extracellular fluid. Intracellular membranes may also have asymmetry. Since the phospholipids are essentially undistinguished, the long term (i.e., over distances of tens of Angstroms) ordering of the membrane along its surface is related to arrangements of the protein components and the polar end-groups of the phospholipids. Some of the proteins or protein structures which extend through the membrane provide channels which allow ions, such as sodium, potassium and chloride to readily cross, or to be selectively controlled or pumped. The size of the channel allows selectivity between differing ions, e.g., sodium and potassium.

The tertiary configuration of the proteins (the three dimensional structure of a single protein molecule), and quaternary configuration of peptide structures (the spatial interaction of separate molecules) are thus critical for proper protein insertion in the membrane, and protein functioning. Thus, the membrane is ordered, and this ordering relates to its function. A disruption of the ordering affects the cell function, and may destroy the cell, or have a lesser damaging, distinct or selective effect.

The membrane fluidity may be controlled by fatty acid composition. For example, bacteria use this mechanism. The fatty acid chains of lipid molecules may exist in an ordered, crystal-like state or in a relatively disordered fluid state. The transition from the ordered to disordered state occurs when the temperature is raised above a "melting" temperature, or more properly, a glass transition temperature. In the case of fatty acyl chains within the membrane, the physiological state is fluidic. Of course, the membrane structure may have a number of different glass transition temperatures, for the various components and their respective energetically favorable orderings which may exist. This glass transition temperature depends on a number of factors, including the length of the fatty acyl side chain and their degree of unsaturation. Unsaturation (with the naturally occurring cis-oriented carbon—carbon bonds) " causes kinks" in the side chains, and increases bond rotation on either side of the unsaturation, both of which impair orderly packing, thus reducing crystallinity and increasing the glass transition temperature. Long fatty acyl chains interact more strongly, stabilizing the structure, and in increase in their proportion leads to a decrease in glass transition temperature.

Higher organisms have cholesterol in their membranes, which increases membrane fluidity. The cholesterol content may be controlled to control fluidity.

It is known that in *E. coli*, the ratio of saturated to unsaturated fatty acyl chains in the cell membrane decreases from 1.6 to 1.0 as the temperature decreases from 42° C. to 27° C. This decrease in the proportion of saturated residues is believed to prevent the membrane from becoming too rigid at lower temperatures. Higher species, including mammals, regulate cell membrane fluidity through cholesterol content, although this mechanism is believed to be absent in bacteria. It is believed that these membrane-composition accommodation mechanisms are comparatively slow.

It is also believed that organisms, such as bacteria, maintain their cell membranes a number of degrees below an important glass transition temperature of the membrane, thus assuring a balance between membrane fluidity and crystalline-like ordering. This crystalline state also implies a non-linear response of the membrane to temperature variations around the glass transition temperature.

Cellular mechanisms are believed to be present which assure that, through commonly encountered temperature variations, irreversible cellular damage does not occur. Some of these mechanisms are active or controlled, and thus have a latency. Some of these temperature changes may also trigger physiological cellular responses, such as so-called temperature shock proteins. Some of these mechanisms are physical and passive, and thus occur relatively rapidly. These include stretching, membrane shape changes, and the like.

According to this theory, the system and method according to the present invention seek to take advantage of these delayed responses in the accommodation mechanisms to temperature increases, by increasing the temperature, through this glass transition temperature, at such a rate that the cellular mechanisms do not have a chance to effectively respond, thus allowing irreversible damage to the bacteria, presumably through a disruption of the higher levels of organization, without necessarily affecting the lower organizational levels of structure. Thus, the temperature of the bacteria need not be raised to a temperature sufficient to thermally denature the tertiary structure of proteins.

Another theory for the observed bactericidal effect, and indeed the sterilizing effect believed to exist, is that, though the temperature of the cells is raised, it is not raised sufficiently to completely fluidize the membranes, leaving them comparatively stiff, brittle or non-compliant. The thermal shock according to the present invention also produces a mechanical stress, which may damage or affect the membrane. This damage may result in lysis, or a less severe mechanical disruption, which may later result in cell death or other response. This mechanical stress may also activate cellular processes or otherwise influence cell functioning. This effect is essentially opposite to that seen in high temperature Pasteurization (HTP), wherein the sustained higher temperatures tend to liquefy the membrane; although these HTP processes are specifically intended to thermally denature proteins to inactivate cells.

High temperature change rates are needed in order to prevent the relaxation of structural changes in a cell, e.g., the cellular membrane, which occur over approximately 10–100 mS. With temperature rise rates in excess of this rate, an effect occurs, which may, for example, disrupt or inactivate bacteria or cells or have other effects.

The induced thermal shock thus produces a number of effects on the cell. First, the cell rapidly expands due to the increase in temperature. Second, the cellular membranes may experience a configurational change either as a primary effect or secondarily due to a phase, volume or shape change of cellular components. Third, while thermal denaturation generally is directed to essentially irreversible changes in the tertiary protein structures of critical proteins and enzymes, thermal shock may effectively reduce quaternary organization to control or alter the cell. Microtubule structures and nucleic acid conformations may also be affected.

According to the present invention, one method for inducing this controlled vet rapid temperature rise is by treating medium containing the cells, generally in relatively small droplets to provide a large surface area to volume ratio and small thermal inertia held at a starting temperature, with an excess of steam at the desired final temperature. The interaction between the droplets and steam is rapid, equilibrating within milliseconds at the final temperature, with only a small amount of dilution due to the high latent heat of vaporization of steam. Generally, in order to reduce a rate-limiting boundary layer, the droplets are degassed prior to treatment.

The water derived from condensed steam chemically dilutes the droplets, rather than mechanically diluting them. In the case of milk, this means that the water is associated with the milk proteins, and the treatment does not substantially adversely affect the flavor of the milk. This excess water may also be removed. In the case of biological media, the dilution is relatively small, depending on temperature rise, and therefore is unlikely to induce a substantial hypotonic shock. However, to the extent that this hypotonic shock does induce a response, that response forms a part of the present invention.

Alternately, other controlled addition of energy to the cell-containing medium or tissue may be used. Thus, a microwave device may be used, which heats the medium through molecular excitation. The power of the microwave is controlled so that the medium is heated to a desired temperature over a desired period. The energy is applied rapidly, in order to obtain the desired temperature rise rate, e.g., in excess of 1000° C. per second, over a short period.

The treatment may also be applied to tissues, since atomization is unnecessary. The use of rapidly applied microwave radiation also means that thermal diffusion or blood perfusion become comparatively insignificant factors in the treatment. The volume to be treated may be physically measured, estimated, or empirically determined by a "test" treatment which applies a relatively small amount of energy and determines the temperature rise in response. In any case, it is important to assure uniformity of treatment of bulk tissues, in order to prevent spatial variations in treatment. However, where the goal is not treatment of all cells within the organ or tissue, for example and organ such as lung, liver or brain, or a tissue such as a solid tumor, then the treatment may be directed toward a portion of the tissue, with care taken not to over-treat any essential tissues. Thus, non-uniform or non-uniform fields of microwaves or infrared radiation (coherent or incoherent, monochromatic or broadband) may be employed to heat cells or tissues.

In general, visible or ionizing radiation and acoustic waves are not generally preferred energy sources because, in order to raise the temperature by the desired amount, other effects will likely be produced in the tissues. However, where these other effects are desired or complementary, they may be employed. For example, ionizing radiation may have a different mechanism for killing or altering cells, where this effect is desired.

A composite treatment may also be fashioned, in which a core tissue is destroyed, while a peripheral shell is partially treated. It is known that one mechanism by which neoplastic cells escape normal immunological surveillance is by hiding antigenic factors from the cell surface, or even not producing certain antigenic markers. It is believed that this aspect of the present invention will overcome these mechanisms are disrupt or alter membranes so that antigenic markers or elements are accessible. In this case, cell death is not necessary for efficacy, as the mere presentation of unique or characteristic antigens may be sufficient to spur an immunologic response which results in an effective treatment.

Blood presents certain interesting properties material to its application for treatment according to the present invention. First, it may be transferred to an extracorporeal reactor. Second, blood components may be separated in real time, in a plasmapheresis process, and individual blood components (erythrocytes, leukocytes, platelets, plasma, etc.) treated separately. Third, it is a liquid which maybe separated into small droplets. Thus, blood treatment may be effected through the steam chamber, using treatment parameters which do not coagulate or denature blood proteins. Generally, a useful blood treatment does not attempt to kill all blood cells, or one would simply extravasate without reinfusion, or separate undesired cell components and not reinfuse undesired components.

Therefore, often a goal of therapy is either selective treatment of a subpopulation of the cells, or a non-lethal treatment applied non-selectively to all or some of the cells present In order to effect a non-lethal treatment, the temperature rise rate is controlled, and/or the temperature rise and/or maximum temperature is controlled.

Blood treatments may be effective, for example, to treat chronic fatigue syndrome (CFS), acquired immune deficiency syndrome (AIDS), malaria, babesiosis, other viral, bacterial, fungal or parasitic diseases, leukemias or other blood-borne neoplasms, blood dysplasias and dyscrasias, immune disorders and syndromes. Bacterial-associated autoimmune mediated disorders, such as those related to spirochetes (syphilis, Lyme disease), as well as other autoimmune related diseases, such as rheumatoid arthritis and lupus, may also be subject to treatment according to the present invention. This later treatment may be applied, for example, to lymphocytes, which mediate immune responses.

In some syndromes, viruses play a primary or ancillary role. Many types of viruses have a lipid coat, which is, for example, derived from the cell membrane of a host cell before budding or lysis, generally with viral-specific proteins or glycoproteins. It is characteristic of chronic viral infections that the viruses avoid vigorous immunological response by not presenting antigenic proteins, or by mimicking host proteins. On the other hand, some chronic viral infections produce an autoimmune response which does not particularly target or eliminate viral infected cells. In either case, the temperature shock method according to the present invention allows relatively mild reconfiguration of membranes, allowing normally unavailable antigenic markers of membrane proteins or intracellular proteins to be presented to the host immune system. For example, a cell membrane inversion may take place, presenting internal antigens. Thus, any disease which is characterized by deficient or misdirected host immunological response is a candidate for treatment according to the present invention. Accordingly, cells which are accessible through the blood, skin or in particular organs may be targeted with the temperature shock treatment.

It is also noted that temperature shock may be used to redirect the activities of a cell. For example, circulating immune cells may be refractory or hyperstimulated. A treatment according to the present invention may be used to "resynchronize" or reset cells to obtain a normal response. Thus, the present invention need not be directed to the treatment or destruction of abnormal cells, but rather to the use of temperature shock for a variety of purposes.

Since the treatment of an individual patient does not necessarily require high throughput, other energy sources may be used, besides steam and microwaves, including general infrared, laser, maser, and chemical sources. Therefore, for example, a stream of blood, or blood component(s), may be subjected to a controlled low power $CO_2$ laser or microwave treatment to effect the temperature shock treatment. Further, using cell separation techniques, such as those developed by Coulter Electronics, Hialeah, Fla., individual blood cells may be separated and individually treated, based on an identification of type, and then, for example, reinfused into the host.

The cell treatment methods according to the present invention may also be applied to in vitro techniques in order to control cells or select cell subpopulations. Typical applications include, for example, genetic engineering clonal selection for temperature shock resistance genes, which may be either a primary goal or a marker gene for a linked trait.

Another organ of interest is the skin, which may have tumors (malignant melanoma, basal cell carcinoma, etc.), psoriasis, viral, bacterial or fungal infection, inflammation, other immunological or autoimmune disorder, loss of elasticity, angioma, and other conditions. The skin is of particular interest because of the ease of external access to the surface. Therefore, for example, a stream of steam, laser beam or infrared source may be applied to the skin, in a manner which would quickly raise the temperature or the surface and possibly a region below the surface. In contrast to types of known treatments, the temperature rise is carefully controlled to avoid ablation or burning, while the heating is nearly instantaneous. The careful control is exerted, for example in the case of steam, by controlling the partial pressure of the steam and performing the treatment within a controlled environment, such as a hypobaric chamber or enclosure. In the case of laser, the pulse energy and repetition rate, as well as particular wavelength of the laser, e.g., $CO_2$ with 10.6 $\mu$m wavelength, may be empirically determined for an effective treatment. In the case of other electromagnetic waves, the field strength and duration of exposure are carefully controlled to effect a desired treatment.

The RTCP Process

The technologies include the use of an apparatus which atomizes a fluid to a uniform small droplet size and subjects the droplets to a treatment. The process treatment passes the droplets through a steam chamber at controlled temperature, which results in a rapid heating and thermal equilibrium of the droplets. The droplets are expelled from an atomizer nozzle at high velocity, so that the residence time in the steam chamber is limited. Since the maximum temperature is tightly controlled, this allows precise treatment parameters based on droplet size, velocity, steam temperature and pressure, and the presence of gasses other than water vapor. The treatment also is influenced by the deceleration of the droplets after treatment, a small dilution factor due to condensed steam, and the cooling of the fluid droplets after treatment.

The equilibration to the steam temperature is so rapid, in fact, due to the high latent heat of vaporization of steam, that a thermal shock is generated in the droplets. This rapid rise in temperature is accompanied by a mechanical expansion, which generates a mechanical shock wave in the droplet. The steam condensation also produces an osmotic "shock", with up to 10–15% dilution, synchronized with the thermal-induced shock. Finally, the droplets are atomized, pass through the steam chamber at a velocity of about 20 meters per second, and are decelerated, for example by impact, resulting in a further synchronized mechanical shocks.

This technique has been shown to kill bacteria and spores with maximum process temperatures of 45–55C, under conditions which do not significantly denature milk proteins or most intracellular proteins. Thus, this technique is now being developed for commercialization as an effective milk sterilization technique. Bacterial cells subjected to this process and which survived were found to have persistent morphological changes in colony growth, which may indicate genetic or regulatory response to the RTCP process.

Using a Pasteurization system according to the present invention, many log reductions in *E. coli* were achieved, for example a reduction of from $10^6$ per milliliter to the limit of detectability was achieved. Bacterial spores (*B. subtilis*) are also reduced, although possibly with lesser efficacy, for example a two log reduction (1% of original concentration) is achieved. It is believed that further refinement of the present system and method will prove more effective against these spores, and prove effective to kill or produce a response in various types of viruses, bacteria, fungi, protozoans, animal cells, and plant cells. The existence of organisms which survive treatment is clear evidence of the gentleness of treatment, and therefore that the treatment may be modulated to effect various survival fractions, and selective treatment of cell populations.

While strains which are desired to be treated may be found which are resistant to the system and method according to the present invention, supplemental methods may also be employed to treat the same medium, such as pulsed electric fields, oscillating magnetic fields, electron ionizing radiation, intense light pulses, actinic light or other visible or ionizing electromagnetic radiation, and high pressure treatments. Thus, treatments may be combined to effect complete Pasteurization or sterilization or more selective cell changes. See, Zhang et al., supra, Mertens et al., "Developments in Nonthermal Processes for Food Preservation", Food Technology, 46(5):124–33 (1992), incorporated herein by reference.

The parameters of a bulk medium steam treatment process which control the efficiency include starting and ending temperatures, steam overheating, rate of temperature rise, degassing procedure (if any), pressure, pre- or post-treatments, pH, droplet size and distribution, droplet velocity, and equipment configuration. Presently, systems operable for milk Pasteurization have been tested using various parameters. For example a test has been conducted with a temperature rise from about 46° C. to about 70.8° C., with a milk pH of 6.60 (start) to 6.65 (finish), and a dilution of 2.5%. Droplet size is preferably about 0.2–0.3 mm. The rate of temperature rise is, for example, in excess of 1500° C. per second, and more preferably above 2000° C. per second. Under these conditions, with a starting bacterial and spore concentration of 10,000 spores per ml, the final concentration was 12 per ml. Thus, a reduction of about three logs was achieved under these conditions, without, for example, sedimentation of milk protein or noticeable alteration in taste.

The bulk medium steam treatment apparatus according to the present invention provides a rapid temperature rise by subjecting relatively small droplets of less than about 0.3 mm to dry steam (non-supercritical) at a partial pressure less than about 760 mm Hg. For example, with a low partial pressure of non-condensing gasses (e.g., less than about 100 mm Hg, and more preferably below about 50 mm Hg), the partial pressure of steam is about 0.3–0.8 atmospheres (e.g., about 225–620 mm Hg). The steam is saturated, and thus the temperature of the steam is held at a desired final temperature, e.g., 40–75° C. The steam temperature-pressure relationships are well known, and need not be reviewed herein.

Droplets of medium including cells to be treated are atomized under force through a nozzle, into a reduced pressure reactor chamber containing the steam. Under this partial vacuum, residual gasses are drawn out of the droplet, which may form a boundary layer, reducing heat transfer rate; therefore, it is preferred that the bulk medium to be treated is degassed prior to treatment. Along its path, the droplets contact steam, which condenses on the relatively cooler droplets and heats the droplets through release of the latent heat of vaporization. As the steam condenses, the droplets are heated, until they reach the equilibrium temperature of the steam, at which tine there is no further net condensation of steam. The droplets will not get hotter than the steam in the chamber, so that the steam temperature sets the maximum temperature. However, depending on reactor configuration, the droplets may not reach equilibrium, and thus may reach a maximum temperature somewhat cooler then the steam. Of course, the initial interaction of the droplet with the steam will produce the highest temperature change rate, so that the reactor system may be designed to operate at a steady state which does not achieve equilibrium temperature. In this case, however, parameters should be tightly controlled to assure complete treatment without overtreatment, and thus a maximum temperature above a desired level.

The condensation of steam on the droplets induces pressure variations, or more properly steam partial pressure variations, within the reactor. In order to prevent a buildup of non-condensing gasses through outgassing or impurities, a vacuum pump may be provided which continuously withdraws gas, with a port near the droplet injection nozzle, removing the non-condensing gasses and some steam. Preferably, however, the product to be treated is fully degassed prior to entry into the reactor, and thus there will be little or no buildup of non-condensing gasses which require evacuation from the reaction vessel during processing. The droplet rapidly equilibrates with the steam temperature under the pressure conditions, over a distance of less than one meter, for example within 70 mm from the droplet injection nozzle. The so-treated droplets are then collected, and may be immediately cooled, thus limiting any adverse effects of long-term exposure to the steam temperature.

In one embodiment, the reaction vessel is provided with a number of zones which maintain steady state distinction. For example, in an initial portion, a low absolute pressure is maintained, degassing the droplets. In a subsequent portion, the droplets are contacted with steam, resulting in a rapid temperature rise of the droplets to effect the desired treatment. In a final section, a low steam partial pressure is maintained, allowing vaporization of water from the droplets, allowing flash cooling. In this manner, the time temperature product may be held at very low levels, effecting a rapid temperature increase followed by a relatively rapid temperature decrease. In order to provide separate temperature zones within the reactor, an external energy source within the reactor may be provided, such as infrared radiation source, to maintain steam temperature. Zones may also be separated by baffles which allow droplets to pass, while providing a gas flow restriction.

The steam in one preferred embodiment is provided by a steam generator, which boils, for example, potable or distilled water. This water is degassed prior to use, so that the steam contains few impurities and almost no non-condensing impurities. The steam generator may be at any temperature above the final temperature, e.g., 150° C., as the thermal treatment of the droplets derives mainly from the latent heat of vaporization of the droplets, and very little from the absolute temperature of the steam. Preferably, the steam is saturated, which will define its temperature in a given atmosphere. If the steam is sub-saturation, condensation of steam on the droplets will be impeded. If the steam is supersaturated, it will itself form droplets and impede the process, in addition to diluting the medium. Process temperature control will also be adversely affected, and may be less predictable.

Thus, the mass flow rate of the saturated steam entering into the treatment system (in relation to the product flow rate and any withdrawal of steam or external heat transfer), controls the process treatment temperature. In the case of an over-pressure steam generator, the mass flow rate is restricted to prevent the treated droplets from reaching too high a temperature, or supersaturation conditions.

The steam is injected adjacent to the path of the droplets being treated, to ensure equilibration by the time the droplet reaches the terminus of the reactor. Due to boundary layer effects of the droplet, due to, for example, non-condensing gasses, as well as diffusion limitations, the temperature rise is not instantaneous. However, using the system in accordance with the present invention, it has been found that temperature rise rates in excess of 2000° C. per second, or even 7600° C. per second, may be achieved, which are sufficient to inactivate bacteria, and thus will effect may different types of cells and cellular structures.

It is noted that steam has a latent heat of vaporization of 540 cal/ml; therefore, a 5% ratio of steam to aqueous fluid to be processed will result in an approximately 27° C. rise in temperature. The resultant 5% dilution may be inconsequential, or remedied in a later step.

In the bulk medium steam treatment device, the medium is sprayed through a nozzle as a stream of small droplets into a reaction vessel. The size of these droplets is preferably less than 0.3 mm, though if the droplets are too small they may present other difficulties, such as poor trajectory control, e.g., from low inertia loss of velocity, e.g., due to drag, Brownian motion, coalescence, and the like. Further, reduced droplet size may reduce potential throughput. In addition, since, if the droplet is too large, each drop of the medium may not be effectively treated, the droplet size distribution should include only a small umber of larger droplets, e.g. less than 1% of greater than 0.45 mm. Steam, which is produced in a steam generator, from, e.g., potable water, is supplied to the reactor vessel through a nozzle or array of nozzles. Steam condenses on the droplets, giving up its latent heat of vaporization to the droplets. The magnitude of heat transfer during condensation is very high, so that the speed of heating reaches several thousand degrees Centigrade per second. Therefore, in the several milliseconds it takes for droplets to travel through a reaction vessel, the temperature is raised substantially, effecting cellular alteration, e.g., bacterial inactivation, according to the present invention.

The steam is derived from a boiler. Tight control of temperature may require a high temperature boiler with a control valve near the reactor vessel. In other words, in order to ensure adequate flow of steam into the reactor, an excess capacity should be available from the boiler. Control is effected near the reactor, to avoid time response delays or oscillation. The water in the boiler is preferably degassed to eliminate non-condensable components. The boiler may have a superheater at its outlet, to heat the steam over a condensation equilibrium level.

The steam is injected into the reactor vessel through a number of steam injection ports, spaced along the path of the droplets within the chamber, so that the region distant from the fluid injection port maintains a relatively constant water vapor pressure. Thus, depending on the desired conditions, effective Pasteurization may be obtained with as low as between 2–5% by weight steam, condensed on the fluid droplets to achieve the temperature rise. There are temperature gradients in the reactor chamber, primarily near the injection nozzle. Since the steam condenses on the droplets, a partial vacuum is created in the region around the droplet, until the droplet reaches a temperature in equilibrium with the pressure, e.g., around 55° C. at 0.5 atmospheres, and thus the vapor pressure equalizes. At equilibrium, the net condensation ceases, and the droplet remains in equilibrium.

The steam consumption is significantly lesser than in known ultra high temperature Pasteurization processes. Assuming the temperature of heat treatment applied to milk is to 60° C., the temperature of milk upon entering the reaction vessel equal to 6–8° C., then the required temperature rise will not exceed 55° C. It will require about 55 Kcal for the heat treatment of one kilogram of fluid medium. As the condensation heat of one kilogram of steam is equal to 540 Kcal (540 cal/ml), only about 0.1 kilogram of steam will be required for condensation, i.e., only 10% of the mass of the product subjected to processing. Obviously, lesser temperature rises will require less steam.

The treated fluid medium, which has been slightly diluted with condensate, is collected on the bottom surface of the reaction vessel and then is supplied through a special vent into the discharging tank. The collected medium is subjected to a vacuum treatment, evacuating gases (air) and steam from the discharge, thus elating excessive water, cooling the fluid medium through water evaporation, as possibly through an external cooling system. The fluid medium may then, for example, constitute a final product or be used as part of a medical treatment.

In a typical bactericidal treatment system, a temperature rise of a liquid to be treated is from about 25° C. to about 55° C. For example, in a reactor 30 cm high, with a droplet velocity of 20 m/sec, the residence time will be about 15 mS. Thus, assuming an inlet temperature of 25° C. and an outlet temperature of 55° C., the temperature change is 30° C. over 15 mS, or about 2000° C. per second. Typically, the temperature rise will not be linear, nor will equilibration require the entire reactor length, so that the maximum temperature rise rate will be well in excess of 2000° C. per second.

The liquid to be treated may be degassed prior to processing, to prevent accumulation of non-condensing gasses within the steam treatment reactor and resultant alteration of the thermodynamic operating point. Further, by degassing the liquid prior to interaction with the steam, the interaction with, and condensation of, steam on the fluid droplets is facilitated. Preferably, non-condensing gasses are kept to less than about 50 mm Hg, and more preferably less than about 20 mm Hg.

Alternately or additionally to degassing prior to dropletization, the fluid may be degassed within a first region of the reactor, under relatively high vacuum, after atomization, with subsequently reaction with the steam in a second portion of the reactor. Thus, due to the gas withdrawal in the upper portion, and condensation of the steam onto the relatively cooler droplet stream, steam will tend to flow from the second portion to the first portion of the reactor. Preferably, a baffle is provided between the two regions, with a relatively high density of fluid droplets to be treated, present in the transition region between the two portions, so that the steam condenses on the fluid droplets in this region, maintaining the pressure differential while effectively treating the droplets. Thus, steam vapor diffuses toward the fluid injection port.

In general since the treatment chamber vessel operates at a maximum process temperature below 100° C., the pressure within the reactor will be below atmospheric pressure. For example, with an operating temperature of 55° C., the chamber will be held at approximately 0.5 atmospheres, or 380 mm Hg. Thus, the pressure in the chamber determines the operating temperature: if the pressure is too high, the necessary temperature to achieve that vapor pressure of steam increases or steam condenses, raising the temperature of the reactor, and vice versa. This condition is considered “wet”. The control over processing is thus primarily exerted by the net mass flow of steam into the reactor. As stated above, a vacuum pump may be provided which exhausts non-condensing gasses and may also withdraw excess steam, allowing an additional control parameter and further allowing a non-equilibrium steady state to exist. For bactericidal treatment, non-condensing or "dry" treatment conditions are preferred.

The walls of the reactor vessel should be maintained at least at or slightly above the final operating temperature, to avoid condensation of steam on the wall and unnecessary product dilution. This may be done by any suitable heating system.

In fact, a number of methods are available to prevent droplets which are insufficiently treated due to, for example, coalescence into large droplets or statistical variations droplet size during atomization, from contaminating the treated product. For example, the droplets may be electrostatically charged, and then normally diverted from a direct path. Droplets of too large a mass will be diverted less, and may be separately collected. Alternately, an entire stream segment may be diverted if a flaw (untreated or untreatable portion) in the treatment is detected. For example, an optical detector may detect a large droplet traversing the reactor and divert the outlet for a period of time to flush any contaminants. An electrostatic or magnetic diversion system may also be employed to electrostatically charge droplets and then separate large droplets from small droplets.

It is believed that, as long as sufficient steam is present, small droplets will be effectively treated, while the persistence of bacteria contamination through treatment is believed to be related to the existence of large droplets. Thus, by eliminating or preventing large or untreated droplets, the effectiveness of the treatment is maintained.

The reactor may also include a second form of treatment, such as ultraviolet radiation, which may be supplied by ultraviolet lamps illuminating within the reactor. Since the droplets are small, the light penetration will be high, thus ensuring full coverage. Likewise, microwaves or other radiation may me used for auxiliary heating of droplets to the desired temperature, or for an electromagnetic field treatment of the droplets.

Where the fluid to be treated contains other volatile compounds, such as ethanol, such vapors may evaporate from the droplets, especially at elevated temperatures. This produces two effects. First, a boundary layer is created by the net outward mass flow, which may impede steam contact and heating. Second, depending on the temperature and pressure, the heating of the droplet may be counteracted by the loss of heat of vaporization of the volatile component. Therefore, care must be taken to ensure that the fluid droplets do not reach the end of the reactor and pool prior to being raised to the desired temperature, or that the temperature rise rate is insufficient. It may also be necessary to inject alcohol vapor with the steam to maintain equilibrium conditions in the reactor. It is noted that the reactor may also be used to reduce or vary alcohol concentrations of the fluid being treated, by varying the treatment conditions. For example, alcohol vapors may be withdrawn and captured through a vacuum pump, along with non-condensing gasses and some steam. This allows the production of a "light" alcoholic beverage, while killing yeast or other organisms.

It is also noted that various non-biological compositions may have glass transition temperatures in the 25–300° C. temperature range, and therefore the present apparatus may be useful for using steam to rapidly alter a crystalline state of, e.g., these polymers, copolymers, block copolymers or interpenetrating polymer networks. This rapid limited heating may be advantageous, for example, to rapidly initiate a chemical reaction while maintaining a mechanical configuration of a bead, for example, if the time constant for the chemical reaction is comparatively fast with respect to the thermal diffusion time constant. Further, in larger droplets, an external polymerized shell may be formed around an unpolymerized interior.

Modification of Cells

The RTCP technique, under appropriate conditions, has the ability to alter cells, without significant denaturation of most proteins. There are three mechanisms postulated to exert effects on the cells:

(a) Heating

Cells are heated in a rapid (millisecond rise-time) and controlled manner to a desired temperature, and held for a short period. Cooling is slower, on the order of seconds. Millisecond heating causes two potential effects. The thermal expansion wave, as well as differential coefficients of thermal expansion, produce a mechanical stress directed on the membrane or cell wall. The cell membrane may also transition through a glass transition temperature faster than the cell can accommodate, resulting in membrane disruption. For example, the glass transition temperature of dipalmitoyl phosphatidyl choline, by scanning differential calorimetry, is about 41° C. "Physical Properties and Functional Roles of Lipids in Membranes", Biochemistry of Lipids, Lipoproteins and Membranes (1996).

(b) Osmotic Stress

The heating effect is carried out by condensation of saturated water vapor on relatively cooler atomized droplets of medium. The dilution may be in the range of 1–10%, which occurs synchronously with the heating. This osmotic stress also acts on the membrane.

(c) Mechanical Shock

The medium, for treatment, is forced through an orifice, causing uniform atomization as a spray of droplets at high velocity, which pass through a steam chamber, reaching equilibrium temperature with the steam before hitting a distal wall. The atomization and deceleration after treatment both produce significant mechanical stresses on the cell.

In many medical treatments, it may be desired to avoid king the cells, but rather to exert a stress to which the cell responds. In this case, the RTCP system is tuned to provide a controlled thermal effect, limited osmotic stress (associated with the temperature rise), and minimized mechanical stress. Thus, mechanical cellular disruption, an effect which is available through other means, is minimized.

In contrast, where it is desirable to kill cells, each of the effects is maximized, limited by thermal denaturation effects and turbulent alterations of the media. In some cases, killing of a partial cell population may be sufficient, in which case the treatment conditions are modulated to minimize undesired side effects, such as dilution, turbulence, medium protein precipitation, etc. In other cases, it is desired to kill all of a cell population or sterilize the medium. In this case, the treatment conditions are established to kill the desired cells with a desired statistical margin.

It is therefore an object of the present invention to provide a system and method for fusing lipid membranes, comprising the steps of providing the membranes to be fused in a liquid medium; and heating the liquid medium, containing the membranes to be fused, at a rate and through a range sufficient to cause a discrete transition in at least one of the membranes, such that the membranes fuse.

It is also an object according to the present invention to provide a system and method for disrupting lipid bilayers, comprising the steps of providing the lipid bilayer in a polar medium; and heating the polar medium at a rate and through a range sufficient to generate a shock wave in the lipid bilayer to reduce an integrity thereof.

It is a further object according to the present invention to provide a system and method for fusing a liposome with a cell, comprising the steps of providing a liposome and a cell in mutual proximity in a physiological medium; and heating the physiological medium at a rate sufficient and through a range appropriate to cause an abrupt glass transition in a portion of at least one of the liposome and the cell to cause a fusion thereof.

It is also an object according to the present invention to provide a system and method for processing a lipid bilayer structure, comprising the steps of providing a lipid bilayer structure in a liquid polar medium; and heating the liquid polar medium at a rate sufficient and through a range appropriate to cause an abrupt glass transition in a portion of the lipid bilayer structure to alter a mechanical configuration thereof.

One of the membranes may be of a eukaryotic organism, for example a mammal. The cell is preferably a circulating formed blood component, such as an erythrocyte, lymphocyte or phagocyte, or even platelet. The cell may also be an abnormal cell, such as a malignant cell, immortalized cell, cell infected with a bacteria, virus or other intracellular parasite, a cell having a genetic or environmentally induced deficiency or surplus of mineral, nutrient, enzyme or other composition.

The system may be used to treat a single type of membrane-bound structure, a pair of structures, or a mixture of a number of structures. For example, cells may be fused with two or more types of liposomes.

The membrane may also be an engineered structure, such as a liposome or vesicle. The engineered structure may have a specific composition on its surface (outer or inner) or interior. The composition may be a pharmaceutical, nutrient, oxidant or antioxidant, cytokine, enzyme (e.g., glucose-6-dehydrogenase), protein, receptor, receptor binding ligand, receptor agonist or antagonist, hormone, gene regulatory agent, antibody or portion thereof, cytotoxic agent, redox state altering composition, pH altering composition, viral protein, viral receptor protein, nucleic acid (e.g., nucleic acid encoding at least one gene or regulator). For example, liposome containing phosphatidylethanolmines, diacylglycerol, ethanol, short chain fatty acids, and/or lipid peroxides be treated, for fusion with a cell.

After treatment, the product may be stored, for example for hours, days or longer, or further processed or employed in a medical treatment. The product may also be used in industrial or biotechnical processes. The cells an/or medium may be injected or infused into an animal for example intravenous or directed to lymphatic pathways.

During or in conjunction with heat treatment, the membranes or medium may be subject to other conditions, such as oxidizing or reducing agents, antioxidant (free radical trapping) agents, photonic or microwave radiation treatment, turbulence or shear forces, or the like. A non-thermal bactericidal treatment may therefore be applied in conjunction with the heat treatment. The medium may be filtered to remove most bacteria.

As a result of heat treatment, the membrane may be reversibly altered, irreversibly damaged, fused or other alterations, in addition to changes due to components added or removed from the membrane during the process. Thus, a cell may be killed or remain alive as a result of the treatment. One set of embodiments according to the invention achieves sterility, for example killing prokaryotic and eukaryotic cells, including mycoplasma.

According to one object of the invention, two different membrane structures are subjected to treatment, one membrane structure having an effective glass transition temperature below an average glass transition temperature of the other. One of the structures may be homogeneous while the other is heterogeneous, e.g., a mosaic domain structure as hypothesized by Singer and Nichols. The heat treatment my therefore induce a gel to liquid state transition in at least a portion of one membrane. The temperature rise rate may exceed an accommodation rate of the membrane.

The rapid heating may, for example, cause at least a portion of a lipid bilayer membrane to enter a non-bilayer state. The heating may also cause a non-linear change in packing density of molecules forming a membrane. In order to improve the efficiency or selectivity of the process, a cell may be incubated under such conditions as to alter a cell membrane lipid composition.

The temperature rise rate is, e.g., greater than 100 C per second, and may be greater than 1000 C per second. The temperature rise may be greater than 10 C, for example 25 to 40 C, and the maximum process temperature may be less than 55 C, preferably less than 49 C, and possibly as low or lower than 43 C.

The heat treatment preferably does not substantially denature cellular proteins, although under certain conditions, denaturation of at least certain proteins may be desired.

The medium may be a physiological solution, milk from a mammal human milk, milk or blood from a transgenic mammal blood plasma or serum, fermentation broth, water, saline or other fluids.

The heating may be effected, for example, by water vapor or steam, which is preferably "superheated" or "dry" to reduce spontaneous condensation. An inert, non-condensing gas may be present during treatment, or the treatment may be conducted with low non-condensing gas levels. Thus, non-condensing gasses may be added or removed during treatment. The medium is preferably degassed prior to treatment.

The medium is preferably atomized prior to heating. The atomized medium is preferably heated while moving at a velocity of at least about 10 cm/sec, preferably at least 100 cm/sec, and more preferably 1000 to 2000 cm/sec or higher. The medium may be subject to mechanical forces synchronized with and independent of the heating.

The apparatus has, for example, a processing capacity of between about 0.25–125 ml per minute, and preferably a processing capacity of between about 1–25 ml per minute. The apparatus may have a transparent treatment chamber, for example made of glass, e.g., borosilicate glass or of fused quartz. The apparatus may also include an automated or assisted cleaning cycle to achieve sterilization and/or to remove deposits. The apparatus preferably has a control, the control being programmed to detect a treatment aberration.

In one embodiment of the invention, two cells are fused in order to achieve a hybrid. Such a process includes treatment of a malignant or immortalized cell and differentiated cell to result in a cell having differentiated characteristics, such as specific gene products, e.g., a significant secreted gene product, such as an antibody. The resulting cell line may therefore produce, e.g., a monoclonal antibody from an immunoglobulin secreting hybridoma.

Other objects and advantages of the present invention will become apparent from a review of the drawings and detailed description.

BRIEF DESCRIPTION OF THE DRAWINGS

The preferred embodiments of the invention will be explained by reference to the drawings, in which:

FIG. 17 shows two possible mechanisms of membrane fusion; and

DETAILED DESCRIPTION OF THE PREFERRED EMBODIMENT

Figure 1:
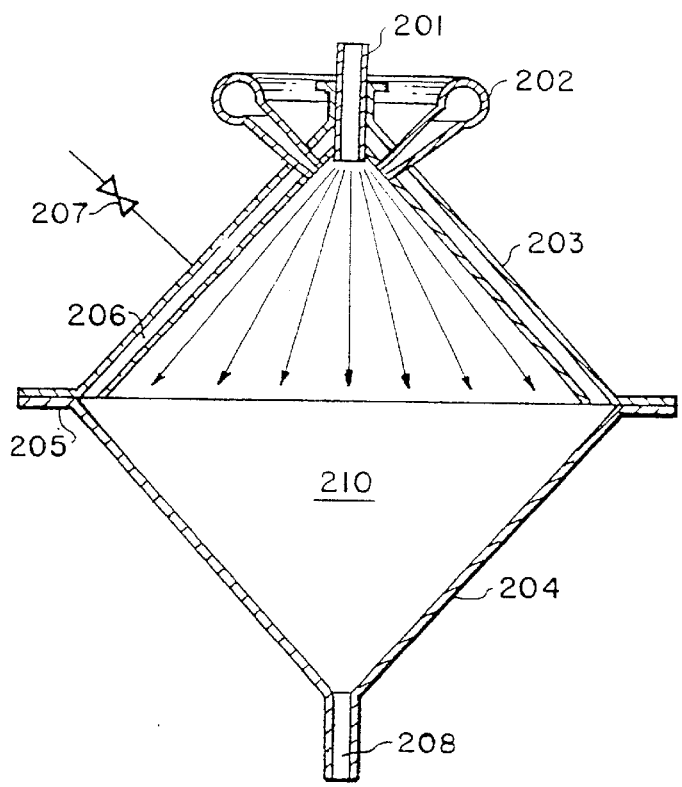
FIG. 1 is a simplified diagram of a reactor according to the present invention.
Figure 3:
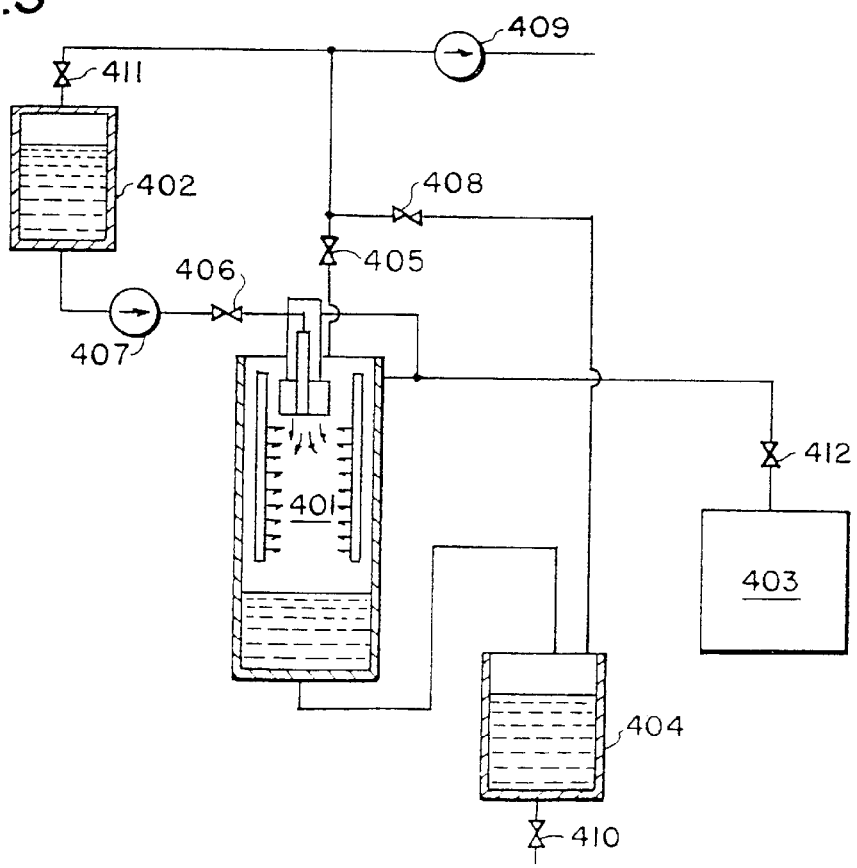
FIG. 3 is a partially schematic diagram of a processing system according to the present invention.
Figure 2:
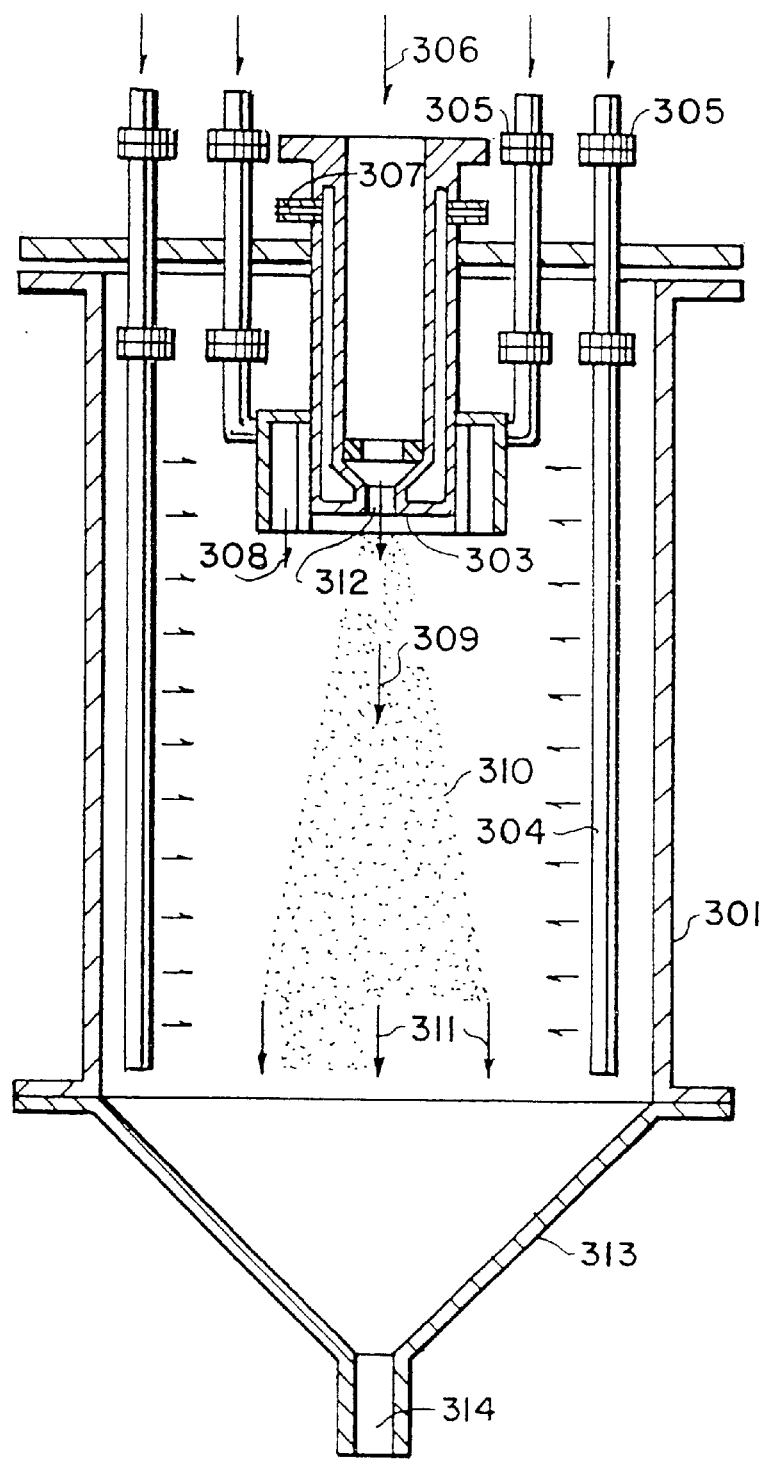
FIG. 2 is a detailed diagram of a reactor according to the present invention.

The preferred embodiments of the invention shall now be described with respect to the drawings, where identical reference numerals in the drawings indicate corresponding features.

EXAMPLE 1

As shown in FIG. 1, the apparatus includes a steam generator and superheater, a pressurizer for the control and test solutions, a degasser, a steam treatment chamber, and a sample collection system.

FIG. 1 shows a simplified diagram of a steam condensation reactor vessel according to the present invention. The reactor is formed of an upper body 203 and a lower body 204, with a seal 205 therebetween. A fluid to be treated, which may be a growth medium, milk, or blood component, is degassed according to conventional procedures, preferably to a level of at most 50 mm Hg non-condensable gasses, and more preferably to a level of no more than 20 mm Hg non-condensable gasses. The degassed fluid enters the reactor at approximately 22° C. through a conduit 201 having an atomizer, which produces a spray of small fluid droplets, dispersed in the reactor space 210. The pressure in the reactor is held at approximately 0.5 atmospheres by a vacuum control system 207, which is provided with a baffle 206 to prevent withdrawal of fluid to be processed. The baffle 206 also serves to insulate the reactor space from the upper body 203. The reactor space is filled with steam, e.g., substantially pure water vapor from steam injectors 202. The steam is provided at equilibrium, and thus the vapor pressure of the steam at the temperature of the reactor, i.e., approximately 55° C., is equal to the pressure of the reactor. Under such conditions, the steam will tend to condense on the fluid droplets, releasing their latent heat of vaporization, heating the droplets, until the droplets reach the temperature of the steam. As the steam condenses, a partial vacuum is created around the droplet, causing a net mass flow into the droplet. Depending on the exact reactor conditions, up to 10% by weight of steam may be absorbed, but generally the amount will be limited to 2–5%.

The droplets are ejected from the atomizer at approximately 20 meters per second. The total height of the reactor space is approximately 30 centimeters. Thus, the residence time of droplets within the reactor, before hitting the lower body 204, is at most about 15 mS. Therefore, the temperature of the droplets rises from 20° C. to 55° C. in about 15 mS, thus yielding a temperature rise rate of at least about 2300° C. per second. In fact, the maximum rise rate will likely be higher, because the steam equilibrates with the droplets before reaching the end of the reactor.

As the droplets hit the lower body 204, an accumulation and pooling takes place, and the fluid drains from the reactor space through exit port 208, assisted by gravity.

FIG. 2 shows a reactor in more detail. The reactor is similar in operation to the reactor detailed in FIG. 1. The reactor is formed of a cover 302, and a shell 301. A lower conical base 313 is provided below the shell 301. In this case, the fluid to be processed is injected through plenum 306, with an atomizer structure 312, which produces, e.g., 5 micron fluid droplets in a fast moving stream 309. Steam is injected through a dual manifold system 305, which includes series of central, upper injection ports 308, which provide a relatively high flow of steam near the atomizer structure 312, and a series of risers 304 which allow for reduced macroscopic pressure gradients within the reactor. In order to prevent undesired preheating of the fluid, a cooling jacket 307 is provided having circulating cooling water around the plenum 306.

The fast moving stream 309 reacts with the steam injected through the upper injection ports 308 and the risers 304, and becomes a heated fluid 310 at approximately the steam temperature. The heated droplets continue through the reactor, and reach equilibrium with the steam, as equilibrated droplets 311, and condense against the conical base 313 and exit the reactor through exit port 314. Preferably, a vacuum is drawn on the exit port to exhaust any accumulation of non-condensable gasses from the reactor during operation, to maintain the reactor in a steady state condition.

Table 1 shows various operating parameters of a preferred reactor design according to the present invention.

TABLE 1

| Parameter | Milk | Vapor |
|---|---|---|
| Flow Kg/hr | 1000 | 100 |
| Pressure in entrance of Processor | 0.4 | 0.1 |
| Steam temperature in Processor, ° C. | 40–100 | |
| Processor volume | 0.1 | 48.8 |

FIG. 3 shows a bactericidal system incorporating the reactor 401. In this case, the fluid to be treated, e.g., milk, is provided in a degassification chamber 402, provided with a control valve 411 to a vacuum pump 409. The fluid is transported with a pump 407, through a valve 406, to the injection plenum of the reactor 401. The reactor 401 is also connected to the vacuum pump 409 through a separate valve 405 for startup cleansing of the reactor 401 and scavenging of non-condensable gasses. Pooled fluid accumulates at the bottom of the reactor 401, and is drawn to a processed fluid holding tank 404, where it may be drained through valve 410. The fluid holding tank is also connected to the vacuum pump through valve 408, to allow a gradient for withdrawing processed fluid from the base of the reactor 401. A steam generator 403 provides steam through control valve 412 to the reactor 401, controlling the temperature in the reactor 401, e.g., between about 40° C. and 90° C., depending on the desired conditions.

EXAMPLE 2

Figure 4:
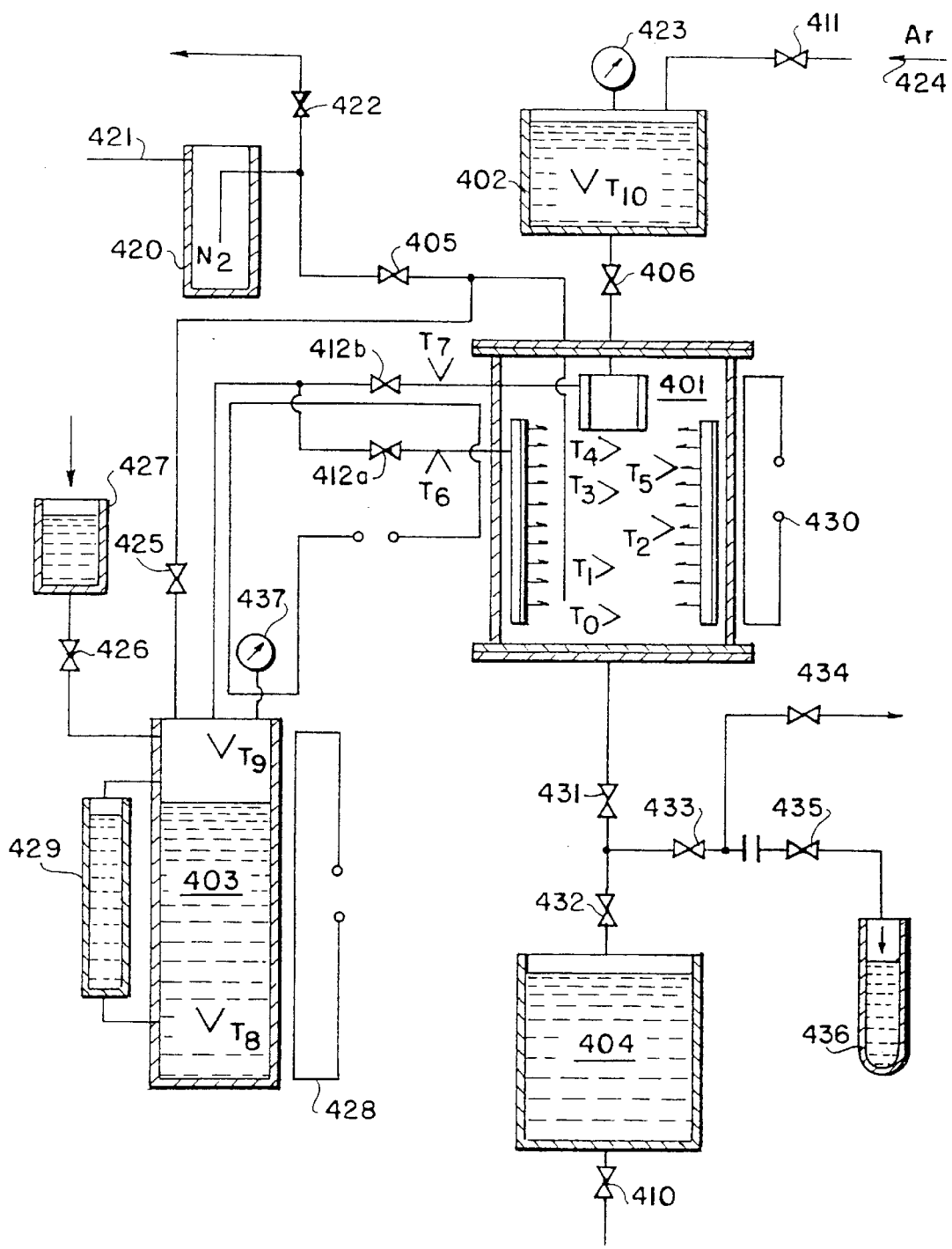
FIG. 4 is a partially schematic diagram of a processing system, showing details of sensor systems for control, according to the present invention.

FIG. 4 shows a bactericidal system similar to the system described in Example 1, with the identification of elements for testing and controlling various conditions within the reactor system. In this system, the steam generator 403 is provided with a sight glass 428 for determining water volume, thermocouples T8 and T9 for determining temperature, pressure gage 437 and an electrical heater 428. Water enters the steam generator 403 from reservoir 427 through valve 426.

The degassification chamber 402, in this instance, shows a system which partially replaces air, with argon 424, through control valve 411. Thus, according to this embodiment, the motive force for driving the medium from the chamber 402 through the nozzle is the argon 424 pressure. While argon 424 is a non-condensable gas, the amount which dissolves is relatively low during a treatment period. A thermocouple T10 and pressure gage 423 are also provided. A heater 430 is provided to heat the outer shell of the reactor 401.

The steam is injected through a pair of control valves 412a, for an annular manifold and 412b, for a riser manifold, into the reactor. A pair of thermocouples T6 and T7 are provided to measure the steam temperature.

Within the reactor, a set of thermocouples T0, T1, T2, T3, T4 and T5 allow determination of temperature gradients within the reactor at steady state conditions.

To maintain vacuum conditions within the reactor, the vacuum pump (not shown in FIG. 4) acts through valve 422 and line 421 through water trap 420 and valve 405. The vacuum also acts through valve 434 to draw pooled fluid from the reactor 401, through valve 431. Valves 432,433 and 435 allow use of sample 436, without disrupting reactor operation.

Figure 12:
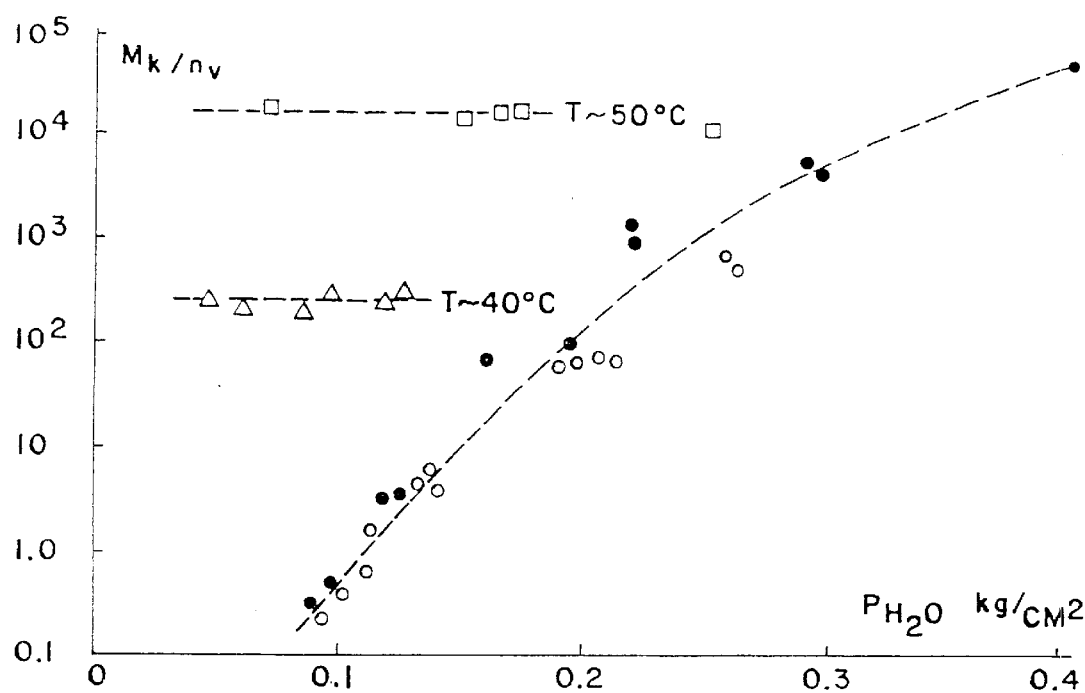
FIGS. 12 and 13 shows reduction of E. coli in milk in the reactor according to the present invention under various conditions.
Figure 13:
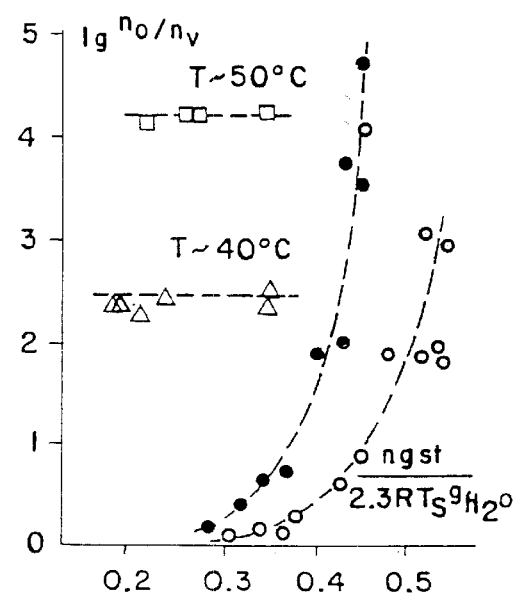

FIGS. 12 and 13 show results of testing the bactericidal effect of the reactor system according to the present invention. In these figures:

$n_0$ is the initial concentration of *E. coli* (FIG. 13)

$n_v$ is the concentration of bacterial which survive treatment $n_k$ is the concentration of killed bacteria $P_{H_2O}$ is the pressure of steam in reactor h is the heat of vaporization of water $T_s$ is the saturation temperature of steam in the reactor R is the gas constant (8.31 g/kg K)

$g_{st}$ is the steam flow $g_{H_2O}$ is the flow of processed liquid

° without degassification of chamber

• with degassification of chamber

□,Δ with degassification of the liquid

FIGS. 12 and 13 thus show that bacterial kill to survive ratios increase with increasing steam pressure (FIG. 12) and that degassification of the chamber improves bacterial Killing as well (FIG. 13). FIG. 13 also demonstrates the effects of the relationship of fluid flow rate to steam flow rate.

Laboratory tests were conducted of various fluids containing *E. coli, B. subtilis* and mixed milk microflora. Tests were conducted of saline solution, milk, egg yolks, and blood plasma. 90% heating of liquid occurred within 1.5 to 2.0 mS. Table 5 shows results of *E. coli* in saline solution. The tests of other bacteria in other solutions produced similar results.

TABLE 2

| Sample No. | End Temp $t$, ° C. | Start Temp $t_0$, ° C. | surviving *E. coli* n, % | initial *E. coli* conc. $n_0$, $10^6$/ml |
|---|---|---|---|---|
| 1 | 50 | 13.2 | 1.4 | |
| 2 | 51 | 13.6 | 1.34 | 0.035 |
| 3 | 52 | 11.0 | 0.1 | 0.035 |
| 4 | 52 | 11.4 | 1.3 | 0.21 |
| 5 | 52 | 11.4 | 1.5 | |
| 6 | 52 | 11.4 | 0.078 | 0.035 |
| 7 | 53 | 23.2 | 1.3 | |
| 8 | 56 | 40.0 | 1.0 | 0.11 |
| 9 | 63 | 37.0 | 0.018 | 0.11 |
| 10 | 64 | 36.5 | 0.027 | 0.11 |
| 11 | 30 | 15.6 | 0.39 | 1.8 |
| 12 | 33 | 20.0 | 0.42 | 1.8 |
| 13 | 40 | 12.0 | 0.006 | |
| 14 | 41 | 24.7 | 0.46 | 1.7 |
| 15 | 42 | 23.8 | 0.37 | 1.8 |
| 16 | 42 | 17.5 | 0.43 | 1.7 |
| 17 | 44 | 19.8 | 0.32 | 1.7 |
| 18 | 50 | 32.8 | 0.007 | 0.22 |
| 19 | 50 | 31.0 | 0.006 | 0.22 |
| 20 | 52 | 30.6 | 0.006 | 0.22 |
| 21 | 59 | 12.0 | 0.009 | 0.21 |

EXAMPLE 3

Figure 5:
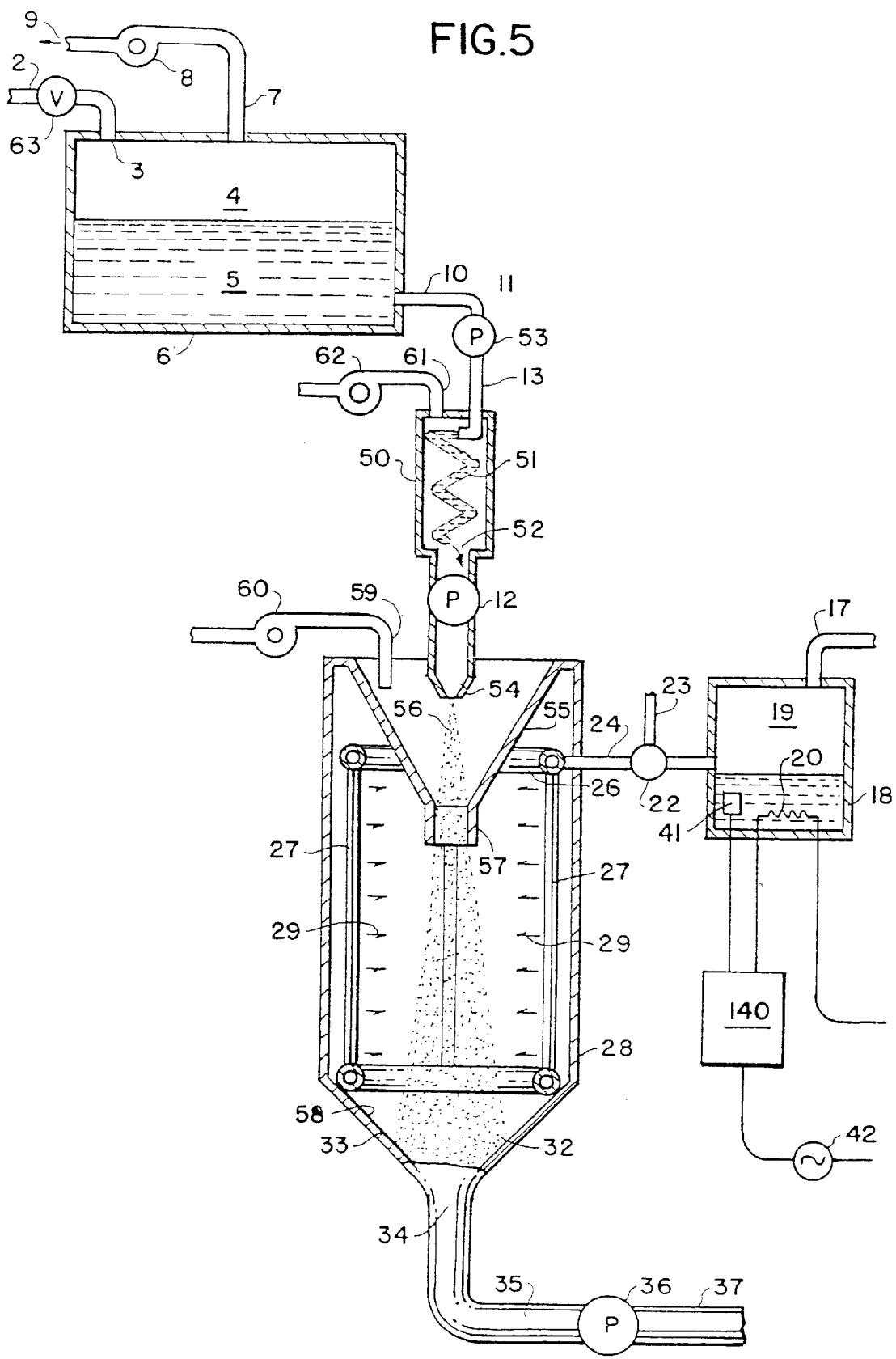
FIG. 5 is a semischematic diagram of a processing system according to the present invention employing continuous mode degassification.

FIG. 5 shows a modified bactericidal system, as compared with Example 1, in which at least a portion of the degassification is performed in-line, rather than in primarily in batch mode. Further, the reactor forms a part of the degassification system.

A holding chamber 6 is provided for milk 5. A partially decompressed gas space 4 is provided, acted upon by a low vacuum pump 8 through vacuum line 7, to vent 9. This acts as a first stage of the degassification process. Fresh milk is fed to the holding chamber through an inlet conduit 2 having a valve 63 and inlet port 3.

The partially degassed milk 11 is fed through fluid feed line 10 to a feed pump 53, through line 13, to a vortex degassification system 50, having vacuum pump 62 through vacuum line 61. The milk 51 swirls under vacuum conditions to exit port 52, and is pumped into the processor with pump 12. The milk is then atomized within the reactor vessel, of the processor shell 28 and the conical pooling region 32, behind a baffle 55. The region proximate to the atomizer 54 is drawn under vacuum by vacuum pump 60 through line 59, to about 20 mm Hg pressure.

The atomized droplets 56 have a high surface area to volume ratio, and degas readily under these conditions. The degassed droplets pass through an aperture 57 of the baffle 55, and enter the main portion of the reactor vessel, coming into contact with steam at approximately 55° C. In this region, equilibrium is not achieved, and a net mass flow of steam will tend to be drawn upward through the aperture. However, since the droplets are cool, i.e., the milk stream is provided at approximately 22° C., and the droplets are further cooled by the degassification treatments, the steam will tend to immediately condense on the droplets, causing a rapid heating.

The steam 29 is injected into the reactor through a vertical steam distribution riser system 27, fed by steam distribution manifold 26, through steam injection line 24, pressure regulator 22, with relief port 23, from steam generator 18 having steam space 119. The steam generator is heated electrically by electrical heater 20, controlled by control 40 with temperature sensor 41 and power source 42. Water is fed to the steam generator 18 through water feed line 17.

Processed milk 58 contacts the conical neck 33 of the reactor and pools 34 at the lower portion, and is withdrawn through outlet line 35, through pump 36, to processed milk outlet 37.

EXAMPLE 4

Figure 14:
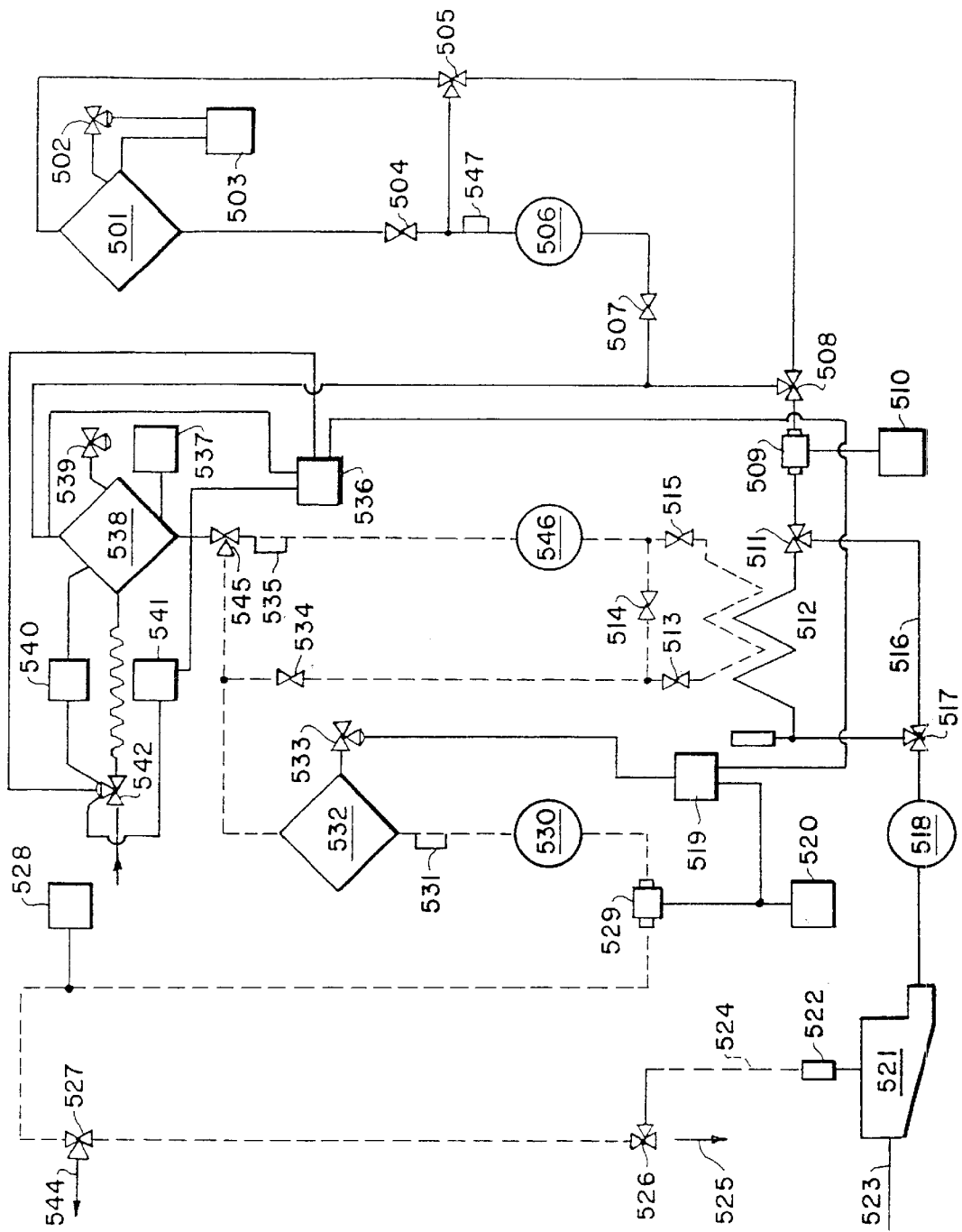
FIGS. 14 and 15 show schematic diagram of a Pasteurizer pilot plant according to the present invention as a flow diagram and process flow diagram, respectively.
Figure 15:
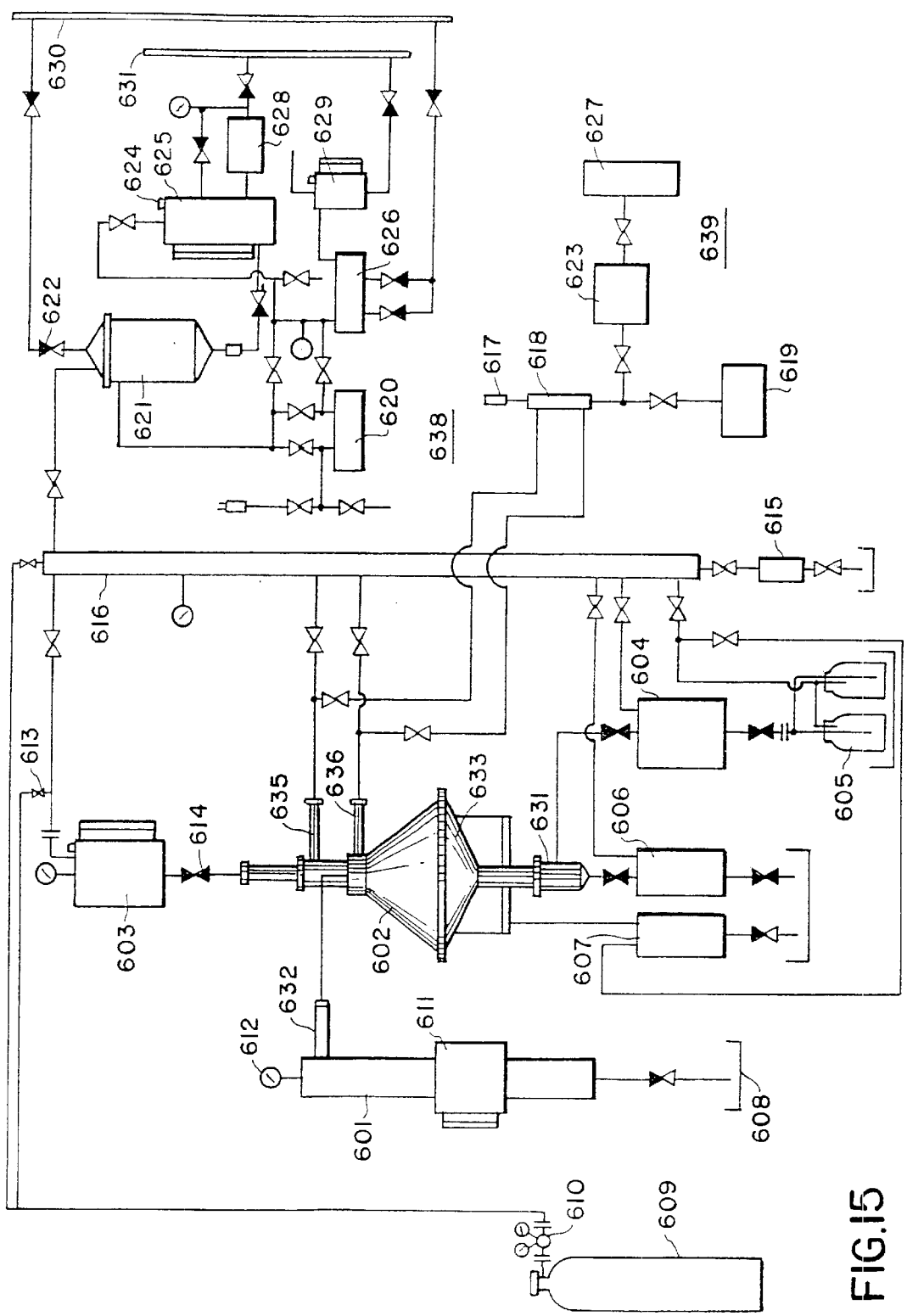

A pilot plant reactor system is shown in FIGS. 14–15. This system allows optimization of process parameters, and is capable of continuous operation, however, as a pilot plant, is generally is operated with a 15 liter fluid reservoir. The system operates on the principle of heating droplets using condensing steam in a vacuum chamber, which is held a constant subatmospheric pressure by a vacuum pump. The pressure within the steam generator is measured with a compound pressure and vacuum gauge 612. The atomization of the fluid is implemented through a nozzle, into which the product is fed under the pressure, for example generated by and inert gas (argon) source, at a pressure in excess of 4–5 atmospheres, through gas/vacuum valve 613. The level of water within the steam generator may be determine by viewing the glass level gauge 611.

The major components of the system, exclusive of controls, include a steam generator 601, a Pasteurization reactor 602, a raw product tank 603, a Pasteurized product tank 604, a vacuum collector 616, a drain tank 606, a condensate tank 607, and an inert gas feed-in system to the raw product tank 609.

The vacuum system includes water circuit pump 626 and vacuum oil pump 620, which can operate individually or following the scheme: the gasses from the vacuum collector 616 are pumped out to a vacuum pump 620, and/or to a water circuit pump 626. In order to avoid water condensation, or to diminish same, in an oil vacuum pump 620, a steam condenser 621, which has its own water feed-in 622 and feed-out system, is installed between the reactor 602 which undergoes evacuation and the pumping system. The vacuum collector 616 drains to a condensate tank 615.

Product steam processing control feedback is implemented through a thermocouple (<1° C. resolution) and diaphragm pressure gauges (10 Pa resolution). Thermocouples are installed in the water and steam units of the steam generator 601, in the reactor 602 near the nozzle, located near the top of the reactor 602 (seven in all) for the purpose of gauging temperatures in a steam-droplet mixture at the product drain line 631 in the reactor 602, and in the tanks of raw 603 and Pasteurized 604 products.

Pressure is measured in a steam collector 632 and in the bottom part of the reactor 634. In addition, it is possible to sample the steam-droplet mixture from the vacuum lines of the reactor 635, 636 for its subsequent analysis on a mass-spectrometer 623 of the mass spectrometer system 639. The sample to the mass spectrometer 623 is passed through a mass spectrometer sampler tank 618, the pressure of which may be determined by pressure gauge 617. A vacuum pump 619 draws the sample gas into the mass spectrometer sampler tank 618. The mass spectrometer is connected to a magnetodischarge diode cooled pump 627.

Vacuum processing of the reactor 602 during operation is implemented in two locations: in the upper part 635 of the reactor 602, near the nozzle 637 for the purpose of degassing raw product from tank 603; and in the bottom part 636 through the reactor 602, around a system of shields, which is the main passage to the vacuum processing system.

Samples of the processed product are taken directly from the stream of the processed product, into disposable syringes, through the drain line 606 of the reactor 602.

The Pasteurizer reactor system consists of a number of components. A nozzle 637 (sprayer) for atomizing milk or any other liquid product to be Pasteurized, into drops. The nozzle 637 is of a standard, centrifugal, dismantling type. The outlet ring 646 of the nozzle 637 is replaceable, its diameter being equal to 4.8 mm for the water consumption of 1 liter per second at a pressure 0.4–0.5 MPa and 2 mm for the water consumption of 0.15 liters per second. The vortex segment 647 of the nozzle 637 has the following dimensions: diameter equal to 27 mm, with the height of its cylindrical part equal to 6.5 mm. The vortex forming ring 645 has 6 triangular grooves 3.2×3.2 mm at an angle of 45° to the horizontal plane. There is an inlet 648 in the center of the ring 645, the diameter of which is equal to 3.6 mm. When the inlet 648 is closed, the nozzle 637 is operating as centrifugal. When the inlet 648 is open, operates in a jet-centrifugal mode. The jet-centrifugal mode of the nozzle 637 fills the cone practically to capacity at a dispersion angle of 90°. The purely centrifugal mode of the nozzle 637 has the center of the cone empty, but the drops are of more homogeneous dimensions. The nozzle has a non-toxic rubber seal 643.

The body of the reactor, is attached to the shield 704 and the steam collector 705, with inlets of 5 mm in diameter for steam dispensing the reactor. The placement of the inlets and their number are optimized by way of empirical testing depending upon the product consumption and the dimensions of its drops. The upper part of the steam collector 705 includes two welded pipes 720 for dry (or slightly superheated for 10° C.–20° C.) food steam. The non-condensing gas is evacuated through the space between the shield 704 and the outer body 721 of the Pasteurizer reactor 700. Connector 722 serves for evacuating the non-condensing gases from the bottom part of the Pasteurizer reactor 700 when there is no preliminary degassing of the raw product, and the degassing process is combined with deaeration. There is a circular groove 723 in the bottom part 706 of the body of the reactor 700 which serves for collecting and discharging of the condensate, which is forming during steam condensing on the body of the Pasteurizer reactor 700.

The bottom of the Pasteurizer reactor 706 is designed for collecting drops of the Pasteurized product, and its subsequent discharging into the tanks 604, 606, 607. The bottom 706 is sealed with a rubber rope gasket 724. There are tubes 725 designed for discharging condensate from the circular groove 723 located on the body of the Pasteurizer reactor 700 into the additional tank.

Food liquid to be treated in the Pasteurizer reactor 700 is broken up into small drops (diameter of approximately 0.2–0.3 mm) by the nozzle 637, on which steam condensing takes place. The drop heating speed and the efficacy of Pasteurization is better when non-condensing gases are eliminated by way of vacuum degassing.

The siphon 726 is attached to the lower part 706 of the reactor's 700 bottom, and has a welded seal for the thermocouple. The system features a siphon 726 to which a connection point 714 with a rubber ring seal 727, has been welded in the upper part of its body. This rubber ring seal 727 enables sampling of the product be taken immediately at the drain line of the Pasteurizer reactor 700 by piercing it with a disposable syringe.

As shown in FIG. 14, raw product 523 with a temperature, for example of 4° C. is fed into the tank 521 (constant level tank), and then is pumped by the pump 518 through valve 517 into the recuperator 512, where it is heated, for instance, up to 44° C. The heated product is then directed through valves 508 and 505 into the deaerator 501, where it is degassed, with a vacuum through the valve 502. At this time partial evaporation of the product is taking place and it is cooled down, for instance to 34° C. The deaerated product is discharged from 501 through product pump 506. Valve 504 and level sensor 547 provide the level, which is necessary for normal operation of the pump 506. Pump 506 feeds the product through Valve 507 into the Pasteurizer 538. All pumps 518, 506, 546, 530 can have similar parameters: capacity greater than or equal to 1 m³/hour, with a pressure no less than 0.4 MPa.

The Pasteurizer 538 reactor is pumped out, reaching the level of pressure approximately 10 Pa through valve 539, and is filled with dry, non-toxic, saturated steam reaching the level of pressure which correlates with the temperature of saturation, for instance, 68° C. Steam Pressure controller 540, with the help of an automatic steam valve 542, provides steam pressure at the inlet to the Pasteurizer 538 reactor which correlates with the specified temperature of saturation (68° C.).

The product is broken up to drops of specified dimensions, for example, 0.3 mm, and is heated up by steam condensation from 34° C. to, for example, 64° C. The heat-up speed is equal to up to 20–30 thousand degrees Centigrade per second.

Through valve 545 and the level sensor 535, the Pasteurized product is pumped out by the pump 546, and is directed into the recuperator 512 through valves 515, 513 and 514. The product is then cooled down in the recuperator 512 as low as, for instance 24° C. and is further discharged into the vacuum unit 532 through valve 534. Here the product is cooled down due to the evaporation into the vacuum, until it reaches the temperature of the raw product, e.g., 4° C.

The cooled down product is pumped out from the vacuum unit 532, through pump 530, and is fed through a magnetic flow meter 529 and Valve 527 either to the drain line 525, through which Pasteurized product is discharged, or into the recirculation line 524 through valve 526, and then into the constant level tank 521 through sight glass 522.

If the temperature of the cooled Pasteurized product is equal to the temperature of the raw product, then dilution of the product with food steam is approximately equal to zero. The precise balance between the water which is induced into the product and then removed from it, is sustained by the Ratio Controller 519, by balancing gas pressure in the vacuum chamber 532.

During optimization of the Pasteurization system, automatic steam valve 542 has to be monitored by the Steam Pressure Controller 540 at the input to the Pasteurizer 538 reactor, by temperature monitor at the output from Pasteurizer 538 reactor and the thermal shock controller 536. After this system is optimized, this valve will be controlled by one of the mentioned controlling mechanisms (most likely the thermal shock controller 536).

It is feasible to eliminate the preheating in the recuperator 512. In this case the product is fed through bypass 516 and further on into the deaerator 501 and into the Pasteurizer 538 reactor. The advantage of this procedure is that assuming that heat-up speed is equal, the maximum temperature of the product at the output from the Pasteurizer 538 reactor will be lower than in a system having a recuperator 512. The drawback, however, is that the extent of deaeration is reduced.

It is also possible to operate the system without the deaerator 501. In this case, the product is fed into the Pasteurizer 538 reactor immediately through valve 508, while 507 is closed, or through valve 508, valve 505, product pump 506, valve 507, while valve 504 is closed.

If recuperator 512 is not utilized, then there is no need to use product pump 546. In this case the Pasteurized product is discharged from Pasteurizer 538 reactor into the vacuum chamber 532 through valve 545 by the force of gravity.

Using the reactor shown in FIGS. 14–15, the following test was conducted. The reactor system, before operation, was subjected to vacuum conditions by a vacuum water circuit pump for one hour to remove residual gasses, down to a pressure of 14 kPa. The steam generator was degassed by heating to 69° C. for one hour, and then all portions of the reactor were steamed at a temperature of 75–100° C., with the vacuum pump turned off. After steaming, the condensate was discharged from the tanks, and the reactor and steam generator hermetically sealed. The reactor was then subjected to partial vacuum and cooled down to 69° C. The steam heater was set to 150° C., with the steam generator set to 65° C.

A physiological solution was initially processed by degassing for 45 minutes. This solution was then fed through the reactor at a maximum rate of 50 liters per minute. The initial concentration of E. coli bacteria in the solution was $8 \times 10^6$ per ml, the initial temperature 20° C., and initial pH=5.1. After treatment, the bacteria were reduced to 20% of starting values, the final temperature was 47° C., and final pH=6.1. Nine liters of fluid were treated in 36 seconds, with a consumption rate of 0.9 m³ per hour. The fluid was pressurized under argon with 4 atmospheres pressure. The average saturated steam temperature within the reactor was 60° C.

The fluid tank was filled with a physiological solution containing E. coli from a sealed bottle. After fill-up, the physiological solution was evacuated through a vacuum pump for a period of 45 minutes in order to degas the product. Argon was delivered into the source product tank under a positive pressure of 4.0 atmospheres, and the maximum outflow rate, with the control valve being fully open, was established. The duration for discharge of 9 liters of physiological solution was 36 seconds, which corresponds to a consumption rate of 0.9 m³/hr. The initial portion of the processed product, about 1 liter, and the final 1 liter portion were discharged into the drain tank, because the startup and completion periods may induce defects in the treatment or be non-uniformly treated. During the middle portion of the treatment, the product ported into the processed product tank, from which a 0.5 liter sample was taken directly into a hermetically sealed glass vessel.

Upon completion of Pasteurization, the steam generator was turned off, and argon was delivered into the reactor and the product was discharged. After discharge, the system was cleaned with an alkaline solution, followed by rinsing with distilled water. The system was disassembled, examined, subjected to boiling of the disassembled reactor, tanks and removable parts of the vacuum system for 5 hours. After cleaning the surface, the system was reassembled.

Based on an analysis of thermocouple data, it is apparent that heating of the droplets occurs within an interval of 70 mm from the nozzle orifice, with a gradient of 0.55° C. per mm. Due to the high fluid flow rate, and a relative insufficiency of the power of the boiler, the Pasteurization process was non-stationary, with a divergence of P and Ps. The steam pressure in the steam generator during the process was lower than the saturation pressure in the steam generator by a factor of 1.0–1.5 kPa. The temperature in the droplet cone was about 60–50° C., i.e. the steam was wet. As was demonstrated by further tests, wet steam is not conducive to optimal results.

EXAMPLE 5

In order have the system described in FIGS. 14–15 operate in a stationary mode, the following changes were made from the procedure described in Example 4:

(1) The power of the steam generator was increased to 12 BTU, together with a superheater it amounted to 15 BTU.

(2) The centrifugal jet injector, having a nozzle diameter of 4.8 mm, was replaced by a centrifugal jet injector having a nozzle diameter of 2.0 mm, thus reducing flow rate.

(3) The geometry of the steam distributor was changed.

(4) Sample testing was performed using a disposable syringe during Pasteurization.

A test was conducted as follows: Starting conditions: $10^6$ E. coli per ml, temperature 21° C., pH=5.37, fluid volume 15 liters. Final conditions: less than 2 E. coli per ml, .e., $2 \times 10^{-6}$ times the starting amount (the limit of the sensitivity of the detection method), temperature 64° C., pH=6.8. The consumption rate was 150 liters per hour. The steam saturation temperature Ts=65° C., with the temperature of the superheated steam being 77° C.

The tests on the air-tightness of the system before the experiment proved that there was no gas in-leakage. The process was conducted with a temperature in the steam generator being equal to 65° C. The steam in the heater was about 10° C. higher than the saturation temperature. Before injecting the liquid into the reactor, the pumping rate was lowered to such level, so that 10% of the power capacity of the steam generator was expended. When the fluid was injected, the steam generator automatically switched to 100% power mode. The reduced power mode was maintained for 5 min. prior to commencing treatment.

Under these conditions, a stationary mode of operation was achieved for 250 seconds. The difference between pressure in the reactor P and the saturation pressure Ps did not exceed 100 Pa. The temperature gradient at the surface of the cone was 2° C. per mm.

EXAMPLE 6

A standard blood pheresis apparatus, available from Johnson & Johnson, is employed in an extracorporeal reactor system to remove and separate blood components. The leukocyte-rich fraction is diluted 1:10 in degassed 4° C. normal saline, and passed through a reactor similar to that shown in FIGS. 14 and 15, although smaller. For example, the reactor is 120 mm high. Droplets are atomized as 75–100 microns. Steam is injected into the reactor to reach a maximum temperature of 35–40° C. flow through the reactor is about 100 ml per minute. The processed leukocytes are reinfused into the patient. Fluid overload is limited by retaining plasma from the pheresis system, as necessary (which may be reinfused later), and limiting the duration of the treatment. Leukocytes may also be concentrated from the treated stream and excess fluid eliminated.

This treatment may be used to treat blood borne diseases, immunological disorders and syndromes, AIDS, CFS, viral diseases, leukemias and blood disorders.

EXAMPLE 7

Figure 6:
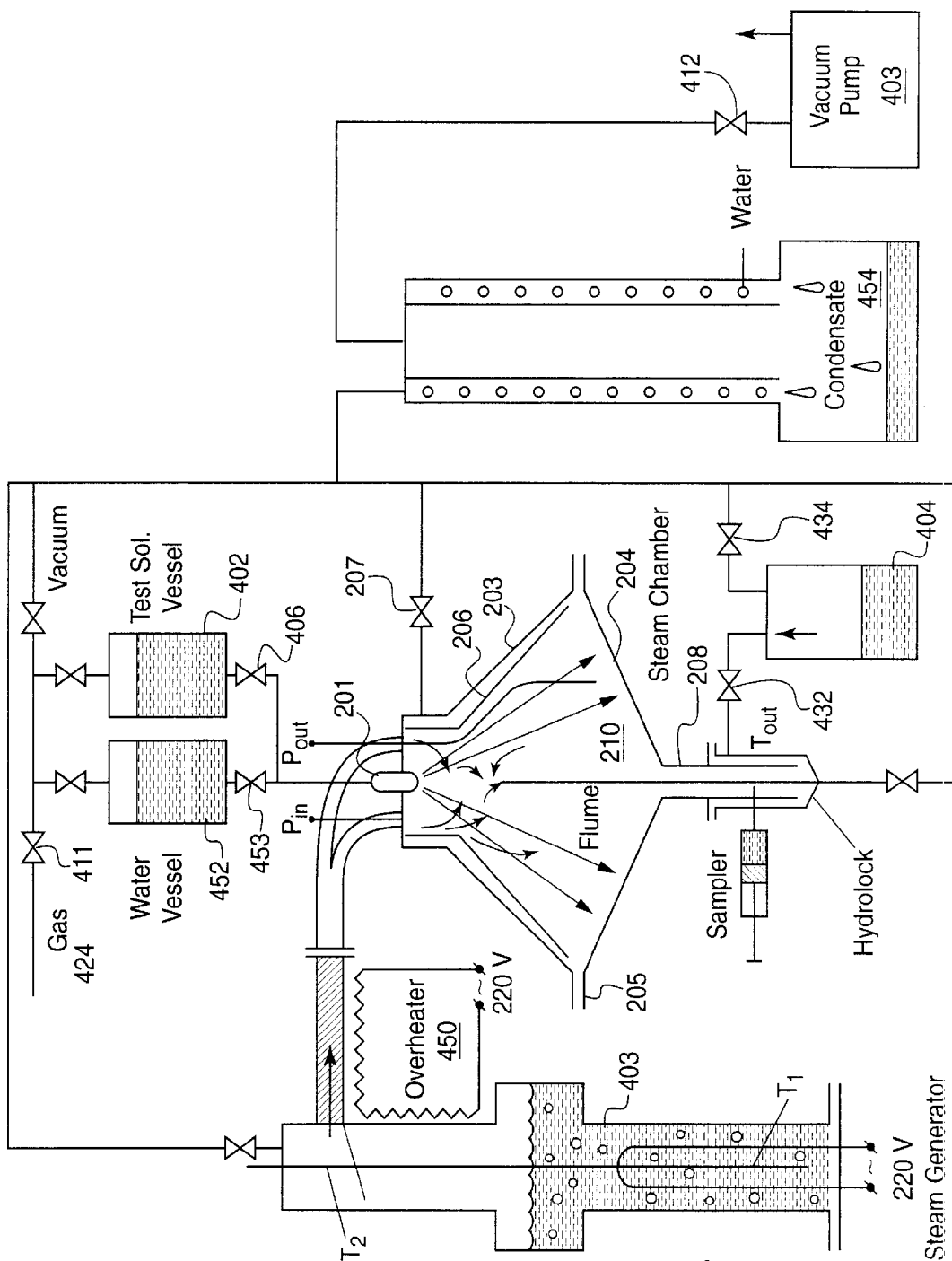
FIG. 6 is a schematic drawing of an RTCP apparatus similar to those shown in FIGS. 1–4.

FIG. 6 shows a modified apparatus generally according to the system described with respect to FIGS. 1–4. The system further includes an overheater 450, for raising the temperature of the steam above a condensation equilibrium, and a sterile solution injector 452 with valve 453 for replacing the contaminated test solution during startup, wind down and during transients, while maintaining steady state operational conditions within the steam chamber. A water cooled condensate collection chamber 454 condenses water before the vacuum pump 403.

Figure 7:
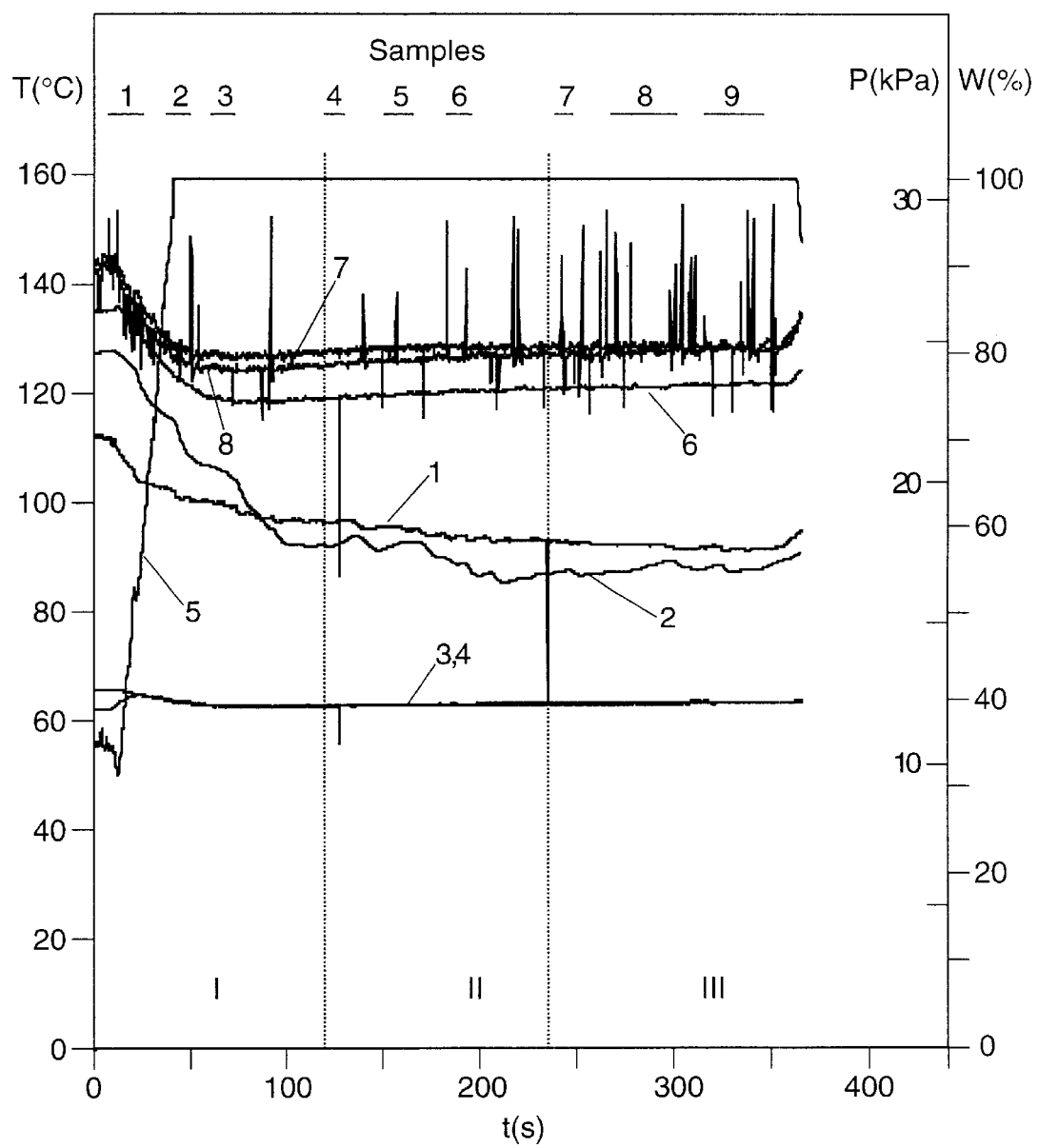
FIG. 7 shows operational parameters of the prototype apparatus according to FIG. 1 operating at 60° C. maximum temperature and overheated steam temperature of about 100° C.
Figure 8:
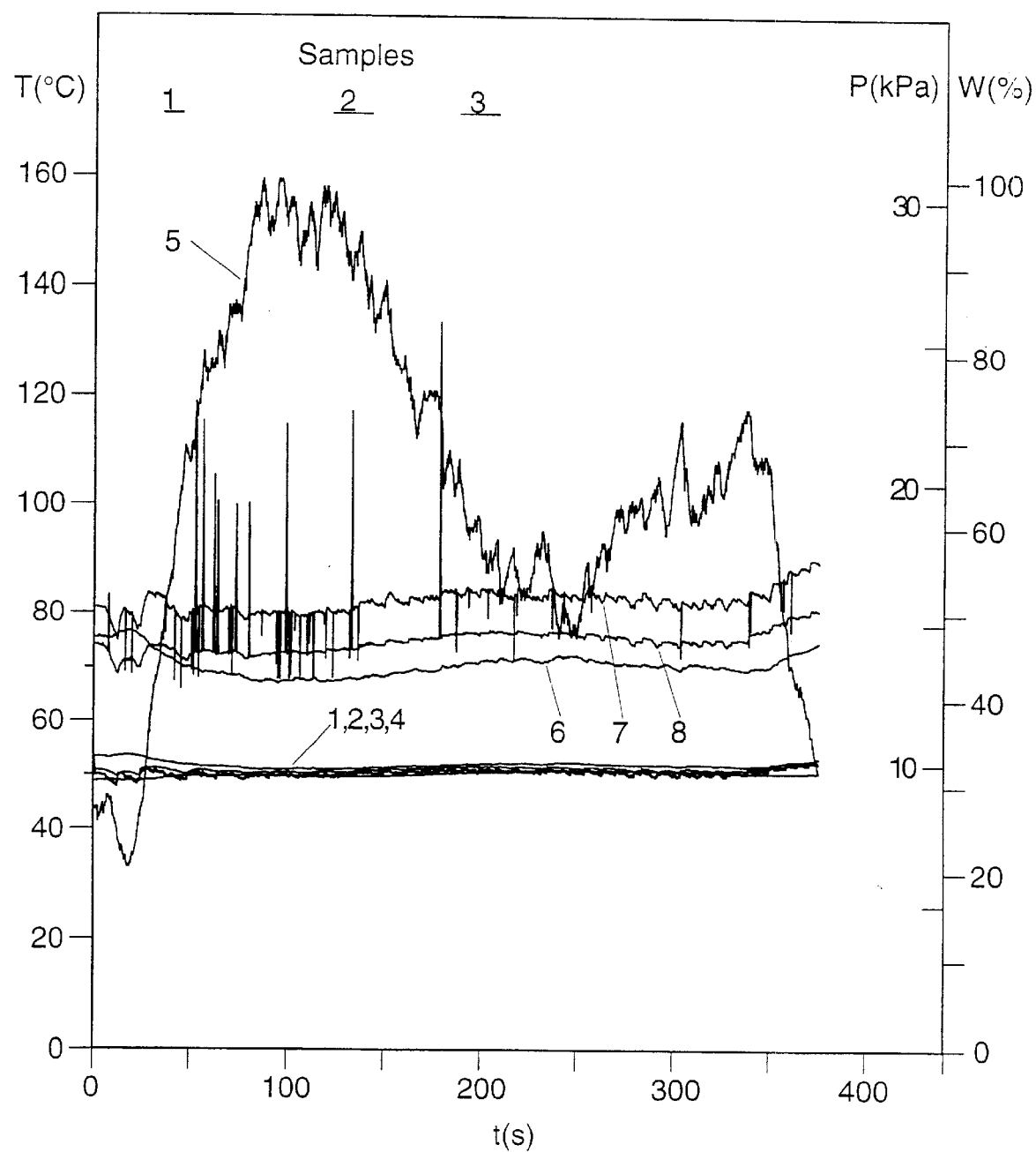
FIG. 8 shows operational parameters of the prototype apparatus according to FIG. 1 operating at about 50° C. maximum temperature.

FIGS. 7 and 8 show results from the testing of the apparatus shown in FIG. 6 with certain parameters:

trace 1 is the overheated steam temperature;

trace 2 is the steam temperature in generator;

trace 3 is the outlet test solution temperature;

trace 4 is the water temperature in steam generator;

trace 5 is the heating power, W;

trace 6 is the saturation pressure, kPa;

trace 7 is the inlet steam pressure, kPa;

trace 8 is the outlet steam pressure, kPa.

EXAMPLE 8

Sterilization of Intravenous Fluids

Intravenous fluids must be sterile on packaging and on administration. Typically, a filtration process is employed to remove all bacteria in the solution. A preservative or antibiotic may also be added to the filtered solution. For saline solutions, this is a highly effective procedure. However, more complex solutions often clog filters and complicate the sterilization process. Further, viruses and a class of cell wall deficient bacteria may pass through filters. Thus, an alternate or supplementary sterilization process may be required.

In solutions having a high protein content, absorption to filter materials may represent a significant loss of active material. Further, traditional heat sterilization (Pasteurization) is not an option due to the presence of heat-labile bioactive components.

The present invention provides a highly effective sterilization process which maintains product potency and reduces production of degradation products. Pyrogens, bacterial cell wall components associated with fever, must be removed from the fluid; however, a filter may be provided, for example before the atomizer, to sufficiently remove pyrogens, without necessarily producing a "sterile" product, free of mycoplasma, for example. The RTCP process is suitable for intravenous stock solutions and premixes, such as antibiotics, immunoglobulins, peptide hormones and factors, serum and plasma, albumin, and other synthetic or natural components.

The RTCP process provides the advantage of a non-chemical, non-denaturing process which may be used to kill typical bacterial, as well as mycoplasma (cell wall deficient bacteria) and viral pathogens.

EXAMPLE 9

Sterilization of Pharmaceutical Products

Pharmaceutical products differ from intravenous solutions primarily in the volume and concentration of an active component. Pharmaceutical products, in particular injectables, usually have a high concentration of active component. These differences lead to a greater incidence of high concentration-dependent reactions between molecules of the drug, as well as precipitation of pharmaceutical product in liquids or suspensions.

There are a number of methods of sterilization now employed, but these may result in toxic residues, loss or denaturation of the pharmaceutical, and may limit throughput of pharmaceutical production.

The process according to the present invention, may be applied both during intermediate stages of production of pharmaceutical products, and to the final product before packaging. The intermediate stage processing may be directed to sterilization or to other controlled effects.

The final sterilization process is provided primarily to assure sterility, and may be provided in conjunction with other complementary sterilization processes, including irradiation, chemical treatments, and filtering.

EXAMPLE 10

Processing of Human Milk for Consumption by Neonates

The RTCP technology is known to be effective in eliminating all or most bacteria and spores from bovine milk. The use of milk treated in this manner for human consumption is the subject of commercialization by a related entity. However, the milk of various species, including humans, has a number of uses besides nutrition.

Human milk contains a number of substances which have been proven beneficial to infant development. However, no technology has been available to store human milk for extended periods or at room temperature without spoilage which would not reduce some of the significant benefits. In fact, to the best of our understanding, no apparatus exists for conveniently sterilizing or Pasteurizing small lots of human milk. Processed milk need not be continuously refrigerated, and will have a shelf life suitable for convenience, travel and to assist working mothers. See, Mestecky, J. et al. (Eds.), Symposium on Immunology of Milk and the Neonate, Miami Fla., Advances in Experimental Medicine and Biology, v. 310 (1990).

Thus, the invention may be embodies in a home human milk processing apparatus employing the RTCP process. The device, for example is capable of processing 20–200 ml of milk in a few minutes, possibly including a sterile bottling adapter. The system is preferably transparent, to allow visible gauging of cleanliness. The device is also preferably portable, powered off line current, fail-safe and self-sterilizing. The device may also be employ automatic or assisted cleaning.

EXAMPLE 11

Processing of Transgenic Milk

Transgenic animals have been used for milk production containing transgenic products. For example, a goat may produce human Antithrombin III in its milk, suitable for purification and injection. A company called Genzyme Transgenics, Framingham, Mass. (www.genzyme.com) is significantly involved in this field. Pharming B.V. (Lieden, The Netherlands) also breeds transgenic animals for foreign protein production in milk. Typically, the transgenic product in the milk is highly purified, so that various sterilization tactics may be employed. RTCP technology, because of its proven efficacy in reducing or eliminating bacterial contamination of milk, while avoiding denaturation of proteins, may be uniquely suited for the processing of transgenic milk in order to retain transgenic protein activity, especially during an early stage of purification.

Transgenic milk may also be consumable by humans, and in this case it is likely that an undenatured form of the transgenic protein would be required in the processed milk.

The apparatus and processing parameters employed for processing transgenic milk would likely be similar to those for the simple sterilization or Pasteurization of milk.

EXAMPLE 12

Processing of Milk By-Products

Cow's milk extract ("mitogenic bovine whey extract") has been found to promote healing of wounds and ulcers. Science, "Healing In Milk", 277:1045 (Aug. 22, 1997). While it is unclear which factors are important in this "naturally derived cocktail of growth factors", the RTCP technology may advantageously be employed to retain activity of peptides during antibacterial processing for distribution of the whey extract as a pharmaceutical grade product.

In fact, at least one company, Immunotec Research Corporation Ltd., has been granted patents (U.S. Pat. Nos. 5,456,924, 5,230,902 and 5,290,571) for the use of undenatured (heat labile) whey protein concentrate for the treatment of AIDS, in order to increase blood mononuclear cell glutathione concentration.

EXAMPLE 13

Cell Fusion with Liposomes

RTCP, due to the potential for controlled heating effects, has the potential to promote membrane fusion. This fusion may be symmetric between two cells or asymmetric between vesicles or liposomes and cells.

A liposome is an artificial structure resembling a closed spherical cell membrane, which may be engineered to have specific membrane lipids, contents, and proteins. Liposomes have been used as artificial reactors for biochemical reactors and as drug delivery systems. Mossa, G., et al., "Liposomes as Bioreactors: Transport Phenomena in Proteoliposomes", Biological and Synthetic Membranes, pp. 227–236, Alan R. Liss (1989); Gregoriadis, G., "Liposomes as a Drug Deliver System: Optimization Studies", Gaber, B. et al. (Eds.), The Technological Applications of Phospholipid Bilayers, Vesicles and Thin Films, Plenum Press, New York (1987); Farmer, M. et al., "Liposome-Encapsulated Hemoglobin: A Synthetic Red Cell", Gaber, B. et al. (Eds.), The Technological Applications of Phospholipid Bilayers, Vesicles and Thin Films, Plenum Press, New York (1987).

Red blood cells, also known as erythrocytes, are circulating blood cells which lack a nucleus. These cells have been extensively studied. Because these cells are suspended in an aqueous media, they have been modified for use as "microreactors", and a great body of literature has developed on the modification of erythrocytes or use of erythrocyte "ghosts" (erythrocytes with their contents replaced with other media). See, Albertini, A., et al. (eds.) Biotechnology in Clinical Medicine, Raven Press, New York (1987); Magnani, M. et al. (eds.), The Use of Resealed Erythrocytes as Carriers and Bioreactors, Plenum Press, New York (1992).

Figure 9:
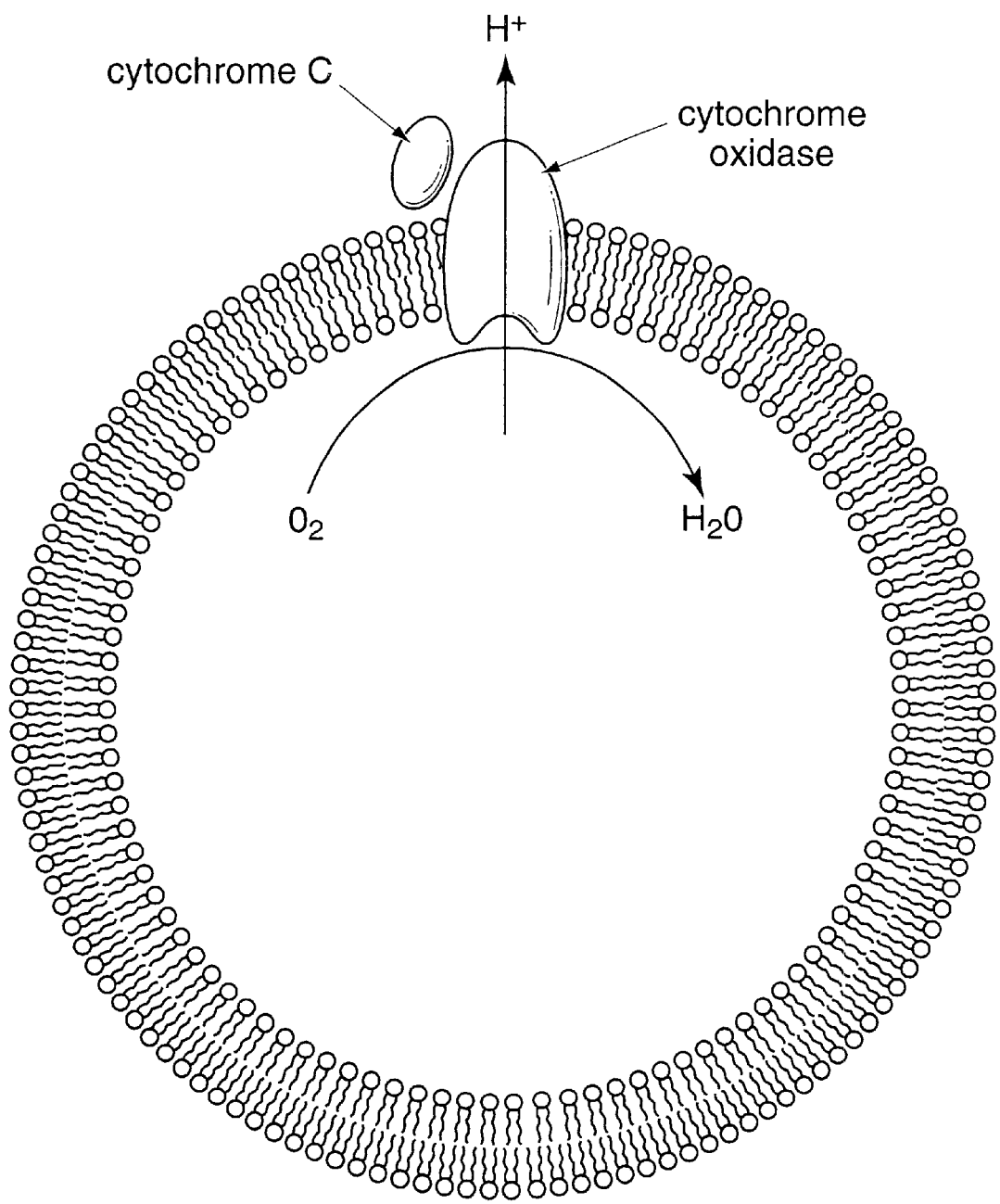
FIG. 9 shows a liposome membrane having cytochrome C inserted therein.

FIG. 9 shows a membrane having cytochrome C, an enzyme, showing how functional systems may be created resembling cellular systems.

The theory behind this cell fusion promoting effect lies in the physics of the lipid bilayer nature of membranes. Cell membranes have a mosaic structure of various regions which have differing characteristics, including lipid composition. Differing lipid compositions are, in turn, associated with different "glass transition temperatures", analogous to a melting point. By raising the temperature of a cell rapidly to a desired temperature for a short period, portions of the membrane may become highly fluid, while other portions remain relatively intact. Thus, the cell structure is maintained. The fluid portions, on the other hand, will become weak and susceptible to other environmental influences, and may enter a bistable state having a non-bilayer structure. Thus, proximity of two membrane portions with at least one in this highly fluidic condition will promote fusion, which is typically thermodynamically favorable, relieving stress on the membrane. The contents of both encapsulated spaces will merge, and the membranes will fuse.

Figure 10:
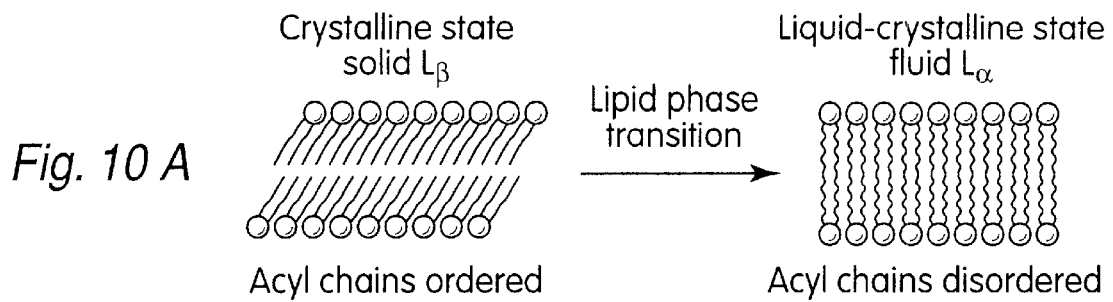
FIG. 10 shows an abrupt phase transition in an experimental system.
Figure 10:
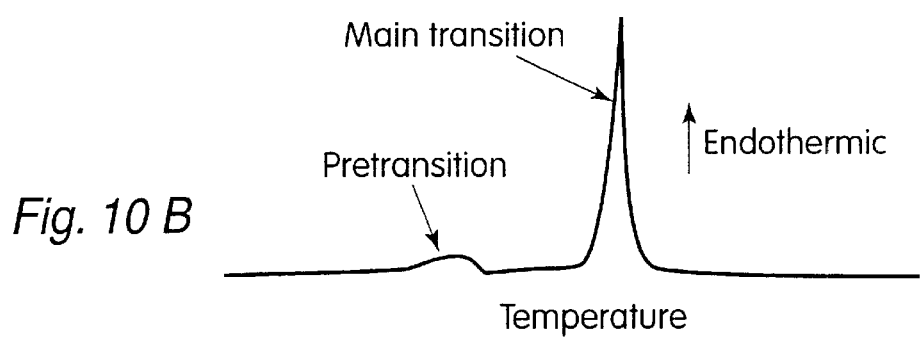
Figure 10:
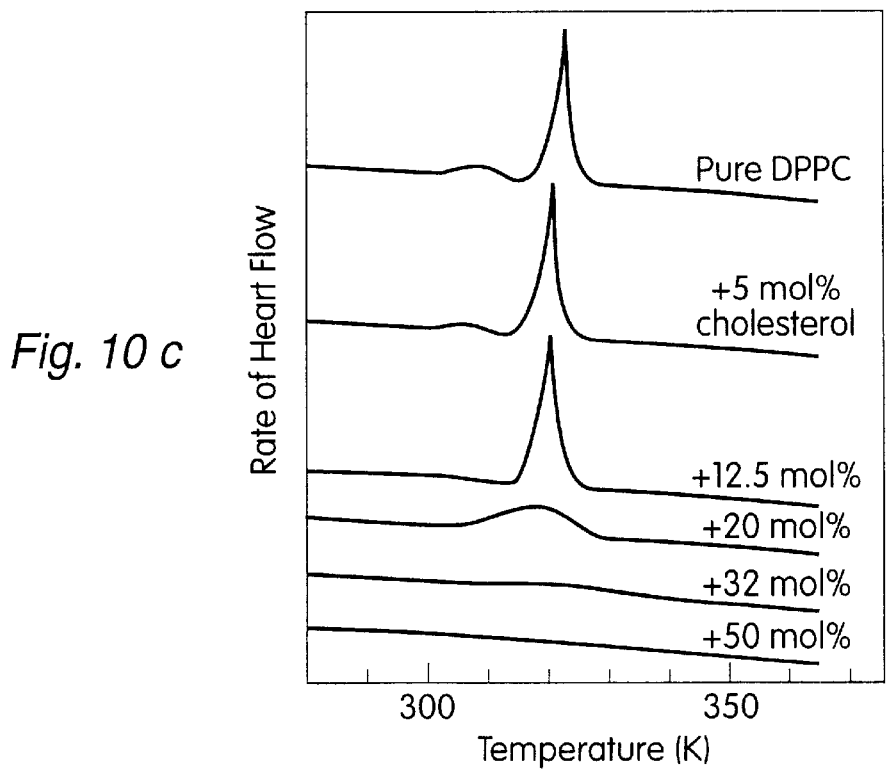

As shown in FIG. 10, this transition, especially in experimental systems, can be quite abrupt.

The Phospholipid gel-liquid-crystalline phase transition and the effect of cholesterol. (A) Phospholipids, when fully hydrated, can exist in the gel, crystalline form (Lb) or in the fluid, liquid-crystalline state (La). In bilayers of gel state PC, the molecules can be packed such that the acyl chains are tilted with respect to the bilayer normal(Lb state). (B) Raising the temperature converts the crystalline state into the liquid crystalline phase as detected by differential scanning calorimetry. For dipalmitoyl-PC the onset of the main transition occurs at approximately 41° C. The pretransition represents a small endothermic reorganization in the packing of the gel-state lipid molecules prior to melting. It is noted that the changes in packing density may be associated with volumetric changes, causing substantial stress when large areas of membrane change phase simultaneously. (C) Influence of cholesterol. The enthalpy of the phase transition (represented by the area under the endotherm) is dramatically reduced by cholesterol, which is present in the cell membranes of higher organisms, but absent in bacteria. At greater than 30 mol % cholesterol, the lipid phase transition seen by this technique is effectively eliminated. See, Davenport, L., et al., "Studies of Lipid Fluctuations Using polarized Fluorescence Spectroscopy", Biological and synthetic Membranes, pp. 97–106, Alan R. Liss (1989).

Table 3 below shows the glass transition temperature for membranes formed of various compositions.

TABLE 3

Temperature (Tc) and enthalpy (ΔH) of the gel to liquid-crystalline phase transition of phospholipids (in excess water)

| Lipid Species[a] | | Tc ± 2° C. | ΔH ± 1 kcal/mol |
|---|---|---|---|
| 12:0/12:0 | PC[b] | −1 | 3 |
| 14:0/14:0 | PC | 23 | 6 |
| 16:0/16:0 | PC | 41 | 8 |
| 16:0/18:1cΔ$^9$ | PC | −5 | |
| 16:1cΔ$^9$/18:1cΔ$^9$ | PC | −36 | 9 |
| 18:0/18:0 | PC | 54 | |
| 18:1cΔ$^9$/18:1cΔ$^9$ | PC | −20 | 9 |
| 16:0/16:0 | PE | 63 | 9 |
| 16:0/16:0 | PS | 55 | 9 |
| 16:0/16:0 | PG | 41 | 9 |
| 16:0/16:0 | PA | 67 | 5 |

[a]The code denotes the number of carbons per acyl chain and the number of double bonds. Δ gives the position of the double bond, c denotes cis.
[b]PC, phosphatidylcholine; PE, phosphatidylethanolamine; PS, phosphatidylserine; PG, phosphatidylglycerol; PA, phosphatidic acid.

Figure 11:
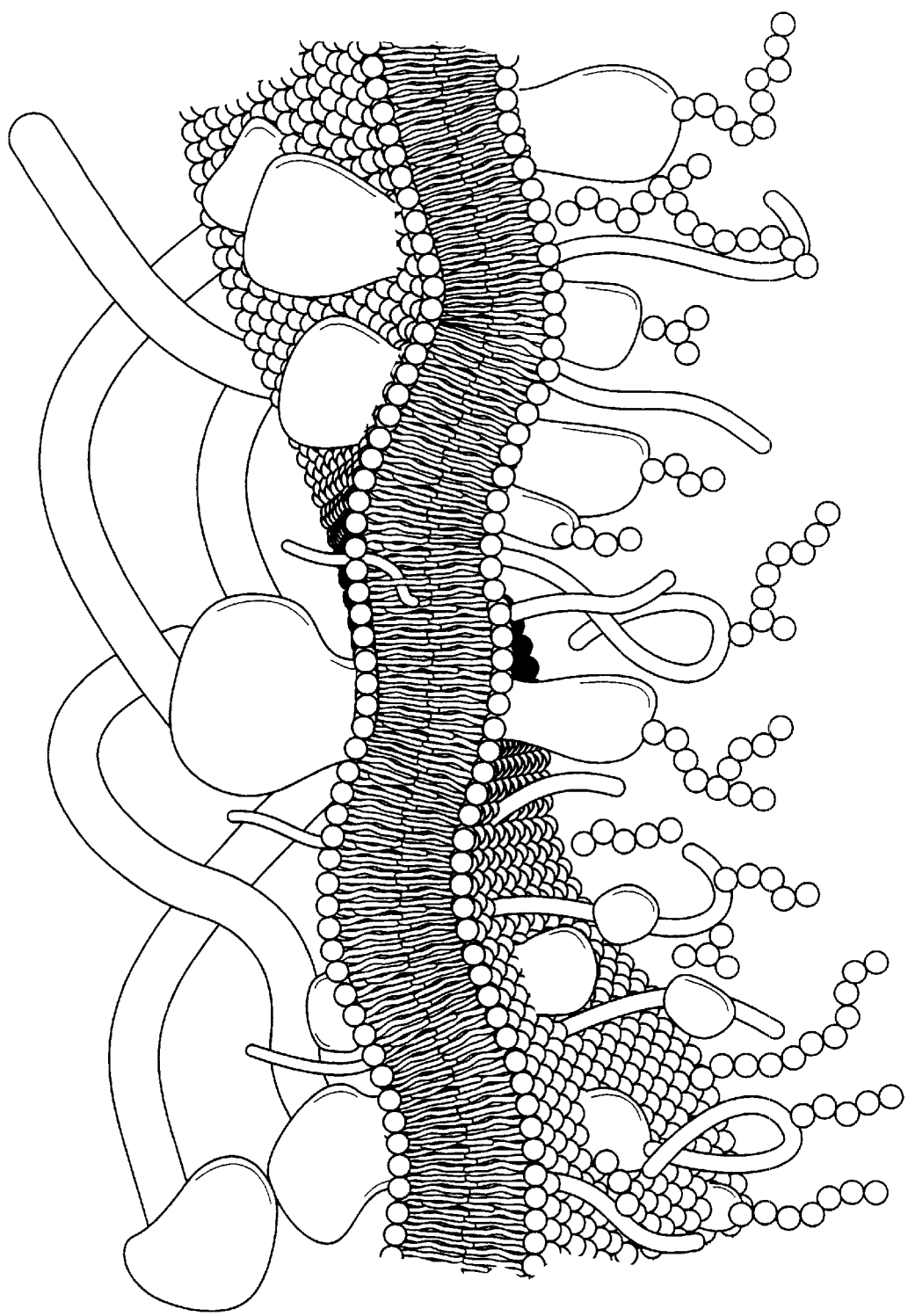
FIG. 11 shows a schematic drawing of a cell membrane.

As shown in FIG. 11, which is a schematic drawing of a cell membrane, the membrane is normally composed of a relatively thin lipid bilayer into which larger protein molecules may be inserted. The proteins alter the microenvironment in the membrane, and thus modify the characteristics of the surrounding portion of the membrane, allowing local differences in properties, such as glass transition temperature, to exist. See, Edidin, M., "Molecular Motions and Membrane Organization and Function", Finean & Mitchell (eds.) Membrane Structure, Chapter 2, Elsevier (1981); Cullis, P. et al., "Physical Properties and Functional Roles of Lipids in Membranes", Vance et al. (Eds.), Biochemistry of Lipids, Lipoproteins and Membranes, Chapter 1, Elsevier (1996); Mouritsen, O. et al., "Protein-Lipid Interactions and lipid Heterogeneity", Watts, A. (Ed.), Protein-Lipid Interactions, Chapter 1, Elsevier (1993).

Figure 16:
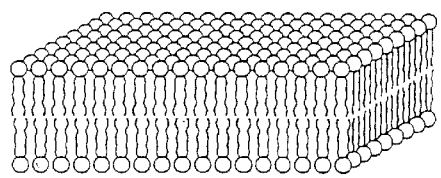
FIG. 16 shows a variety of lipid phases in aqueous medium, including bilayer and unstable states.
Figure 16:
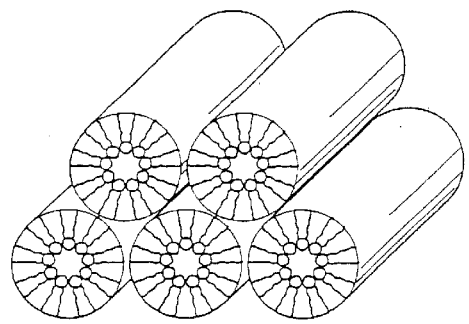
Figure 16:
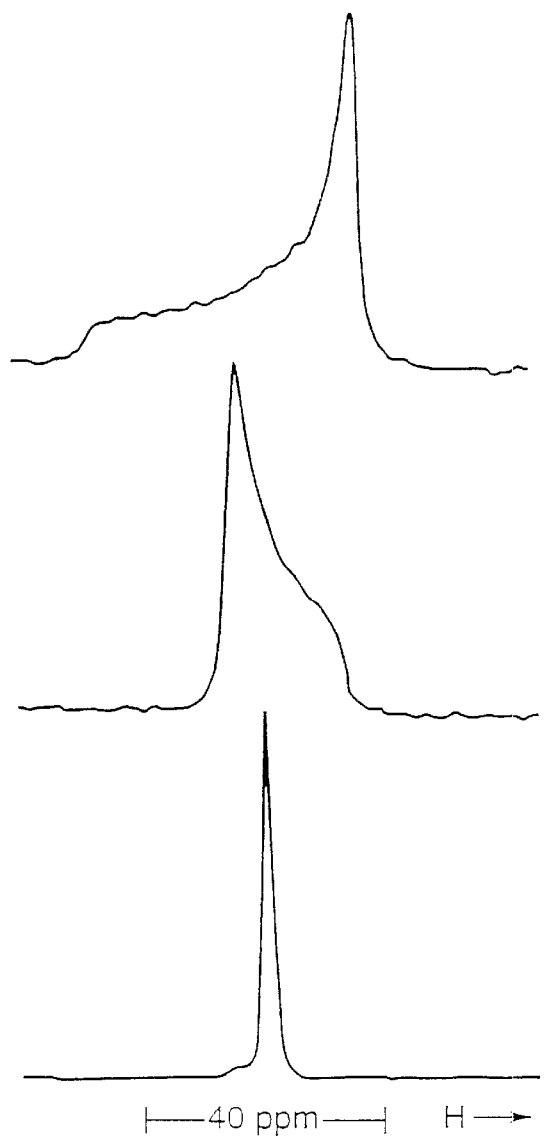

Typically, liposomes are endocytosed by macrophages or reticulo-endothelial cells, preventing fusion of the membranes. See, van Rooijen, N. et al., "Transient Suppression of Macrophage Functions by liposome-encapsulated Drugs", TIBTECH, 15:178–185 (May 1997). However, by RTCP treatment, two membranes in close proximity may be excited and made unstable ("melted") to allow fusion. The type of changes which may occur in the membranes are shown schematically in FIG. 16, along with an NMR tracing showing a change in chemical configuration.

It is expected that partial cellular permeability during treatment will also be apparent, but that the cells will return to normal after RTCP treatment. Excess RTCP treatment, however, may result in massive loss of membrane integrity and cell death. The treatment need not be lethal, and in fact it is believed that under some conditions RTCP may selectively stimulate or activate cells. In particular, cells which have become tolerant to a condition may be subject to "rejuvenation".

Since the liposome is a synthetic structure, the exact composition and characteristics of a liposome may be engineered to assure efficient fusion, which occurs by a process as indicated in FIG. 17.

This process is distinct from the normal processes for clearance of liposomes from the blood. Normally, the liposomes are endocytosed or "eaten" by cells of the reticuloendothelial system (RES), avoiding direct uptake of liposome contents and membrane fusion.

This fusion may be promoted by the use of "receptors" or antibodies which specifically attract the cell surfaces together, a technique particularly appropriate for vesicles or liposomes. These receptors may be, for example, genetically engineered viral glycoproteins. Nonspecific absorption techniques may also be used.

The fusion of a liposome with a cell may be used to alter the characteristics of a target cell, which may be a circulating blood cell, in vitro cell culture, biopsy cell sample, or the like. The surface of the cell is modified by the liposomebound membrane proteins, while the contents of the liposome are released into the cell. One or both of these principals may be applied in any given case.

There are, of course, other known liposome-cell fusion techniques. However, these techniques either involve viruses or viral proteins, which may be pathogenic, toxic or antigenic, or chemicals. Therefore, the RTCP technique has potential for a reasonably safe in vivo treatment, while other known techniques are typically limited to in vitro use.

Liposomes, which have been proposed as drug delivery systems alone, are rapidly and preferentially taken up by the reticulo-endothelial system, thus making them difficult to target to other organ systems. In contrast, normal-appearing erythrocytes are not taken up by the reticulo-endothelial system, and may have an average circulating lifespan of 60 days. Thus, by fusing liposomes with erythrocytes, a long lasting reservoir of drug may be obtained.

It is also noted that there are a number of genetic diseases which are manifest as abnormalities in red blood cell proteins (sickle cell anemia, thalasemia) or metabolism (glucose-6-dehydrogenase deficiency G6DH) The latter disorder is believed to affect 400,000,000 people, and which may result in an anemia, especially in homozygous persons who inherit the defective gene from both parents, and who ingest certain foods. In the later case, for example, a genetically engineered G6DH may be encapsulated in liposomes and the liposomes fused with red blood cells, reversing the deficiency and preventing the premature loss of red blood cells. Treatments would be required, for example, every 30 to 60 days.

However, this technology is not limited to erythrocyte disorders. Otherwise normal erythrocytes may be targeted to a particular tissue, for example by modifying the surface structures. This surface modification may be, for example, by liposomal membrane components. The modified erythrocytes need not be returned to the venous system, and may be presented through the lymphatic system or other body space. By using erythrocytes, or even the patient's own erythrocytes, rejection and side effects are minimized.

A target disease for this type of treatment is chronic viral infection, such as hepatitis (hepatitis B, hepatitis C, delta factor) or AIDS. In order to protect the normal target cells of the viral infection, red blood cells are modified to present viral receptors. Due to the large number of red blood cells, the virus load is absorbed, tending to spare the normal target cells. The red blood cells are not capable of reproducing virus, ending the life cycle. A specific antiviral agent may be provided in the liposomes to further interfere with viral reproduction (in other cells).

It is noted that this treatment would tend to be costly; however, many chronic viral infections cause substantial morbidity and mortality, suggesting an advantage of even costly repeated treatments if efficacy is proven.

EXAMPLE 14

Cell to Cell Fusion

RTCP, due to the potential for controlled heating effects and abrupt changes in temperature, has the potential to promote cell fusion. As stated above, this fusion may be symmetric between two cells or asymmetric between vesicles or liposomes and cells.

The theory behind this cell fusion promoting effect lies in the physics of the lipid bilayer nature of membranes. Cell membranes have a mosaic structure of various regions which have differing characteristics, including lipid composition. Differing lipid compositions are, in turn, associated with different "glass transition temperatures", analogous to a melting point. By raising the temperature of a cell rapidly to a desired temperature for a short period, portions of the membrane may become highly fluid, while other portions remain relatively intact. Thus, the cell structure is maintained. The fluid portions, on the other hand, will become weak and susceptible to other environmental influences, and may enter a bistable state having a non-bilayer structure. Thus, proximity of two membrane portions with at least one in this highly fluidic condition will promote fusion, which is typically thermodynamically favorable, relieving stress on the membrane. The contents of both encapsulated spaces will merge, and the membranes will fuse.

Typically, the membrane structure of cells is difficult to control or modify. However, in vitro cell culture techniques including nutrient broth and incubation temperature, may be used to control membrane composition.

While "receptors" or antibodies may be used to align cells for fusion, typically a non-specific absorption technique might be applied to agglomerate cells prior to treatment.

A typical application for fused cells is the production of monoclonal antibodies. In forming a monoclonal antibody-producing cell line, a B-lymphocyte of a selected clone (e.g., human antigen-specific) is fused with an immortalized mouse cell line, to produce an immortalized (continuously growing) cell line which produces a selected type of human immunoglobulin (hybridoma). In order to produce a desired type of immunoglobulin, hundreds or thousands of cell lines must be individually produced and tested. A more efficient fusion technique may therefore have considerable utility.

A typical use of this technique is the production of tumor specific antibodies as a diagnostic or therapeutic agent. In this case, the antigens on the tumor may vary between patents with the same diagnosis, so that a large library of antibodies must be maintained or a custom production technique implemented. The RTCP technique may therefore be used to generate a large number of candidate clones, which may then be tested with the actual tumor cells and then cultured to produce significant quantities, all within a clinical timeframe. In fact, the patient's own lymphocytes may be used to produce the antibodies, potentially reducing an adverse or allergic response, and increasing the possibility of finding an appropriate clone, given the existing stimulation of the patient's immune system by the tumor.

EXAMPLE 15

Cell Mediated Immune Response Vaccine

In some circumstances, antigens are more efficiently presented by and processed from a cell surface than in soluble or precipitated form. This effect may be responsible for a number of failures of proposed vaccines to effect long lasting immunity. RTCP-induced cell fusion allows recombinant antigens to be presented on a desired cell type, for example erythrocytes, which may activate the body's cellular immune system to produce an effective response.

Thus, a cell, such as an erythrocyte or other sacrificial cell is modified to present a foreign antigen. The antigen may be, for example, gp120 (HIV), HBSag (Hepatitis B surface antigen), or other known antigens, not necessarily related to human disease or deficient vaccine response in humans.

The antigen is provided by fusion of the sacrificial erythrocyte cell with an engineered liposome, as discussed above. Alternately, an artificial cell may be constructed by fusing one or more engineered liposomes with a target, to produce a structure with only the desired antigenic determinants.

EXAMPLE 16

Treatment of Formed Circulating Blood Cells

Formed cells circulating through the blood include red blood cells (erythrocytes), white blood cells (leukocytes), platelets, metastatic and abnormal cells, viremia and bacteremia. The treatment with RTCP may be used to produce a number of different effects in populations and subpopulations of the cells. These treatments include killing or lysis, membrane disruption (reversible or irreversible), membrane component exchange with medium, other cells, or vesicles or liposomes, budding of cellular components, cell fusion or liposome-cell fusion, or other effects.

The RTCP technology, having millisecond temperature rise-times, disrupts or alters cell membranes and larger formed structures, while retaining protein configurations and thus avoids certain protein denaturation.

For example, this RTCP technique may be used to kill bacteria or some viruses in plasma or serum. This killing may be direct, by the known thermal shock mechanism, or by augmentation of MSP with membrane-active compositions which reduce membrane integrity and thus increase cell or virus lysis under the MSP conditions.

Augmentors may include phosphatidylethanolmines, diacylglycerol, ethanol, short chain fatty acids, lipid peroxides, and other compositions. Some of these augmentors are innocuous, may be removed or degraded, or have desired or beneficial effects.

Likewise, treatment conditions may be established which are typically non-lethal for formed cell components, vet which temporarily reduce membrane integrity. This temporary lapse may allow cellular contents to leach into the extracellular fluid, allow extracellular reagents to enter the cell, or allow a reconstitution of the cell membrane with foreign proteins, lipids, drugs or macromolecules.

There has been much research on the use of red blood cells as a vehicle to provide a durable (approximate 60 day average life for a normal adult) reservoir or drug, while, depending on the particular drug, directing release into the liver and spleen or throughout the body. Such drugs might include contraceptive agents, flavinoids, steroids, carotenoids, markers and radionucleides, antifungal agents (amphotericin B), vitamin B-12, antioxidants, such as glutathione and alpha-tocopherol, and other compositions.

The technique also holds promise for reformulating membranes of cells, for example inserting phosphatidyl choline or sphingomyelin, cholesterol in the membrane of erythrocytes, which may reduce uptake by the reticuloendothelial system. Likewise, the concentration of these compositions may be reduced to target the RES. These techniques may also be applied to liposomes, although typically the membrane composition may be defined during production and need not be later altered.

This technique may also offer hope for the treatment of certain diseases in which erythrocyte membrane chemistry is abnormal, for example resulting in fragile cells and excessive hemolysis.

Another disease which is potentially reachable by the MSP process is sickle cell anemia and various other hemoglobin abnormalities. Essentially, the erythrocytes are treated to either exchange hemoglobin with a pool of normal hemoglobin (synthetic or from human or animal donors), or to access the intracellular space of the erythrocyte to change conditions (e.g., pH), to alter oxygen binding characteristics.

The technique may also be used to increase the shelf life of formed blood components, such as by the addition of antioxidants to the membrane or intracellular space, or even the introduction of enzymes necessary for vitality. The later may be effectively achieved by facilitated fusion of a cell with a liposome containing the desired membrane or cytoplasmic components.

This technique also holds promise for gene therapy, in that genetic material may be introduced into cells without viral vectors.

EXAMPLE 17

Selective Processing of Cells by RTCP

Typically, RTCP would not be expected to exert a selective effect on mammalian cells, so that a lethal treatment for one subclass would likely be lethal for the other subclasses. Two strategies are available to increase selectivity of effect, resulting in differential killing or processing.

This possible selectivity is based on the regional mosaic properties of cell membranes, various regions of cells have different glass transition temperatures, as well as mechanical responses to RTCP technology. In order to gain selectivity, the entire population of cells may be subjected to a treatment which selectively increases a response of a selected subgroup to the RTCP treatment, or "hardens" a selected subgroup against RTCP treatment. These treatments thus seek to directly or indirectly selectively alter the lipid composition of cell membranes or the effect of RTCP on the membranes. Selectivity may ensured by simple metabolic distinction, mitogenic factors, other types of selective growth factors, monoclonal antibodies, drugs or hormones. The membrane lipid changes may be effected by altering the growth media while cell growth is selectively stimulated, fusing the selected cell populations with vesicles or liposomes of a desired composition, or employing native cellular mechanisms to alter the membrane composition. See, Horizons in Membrane Biotechnology ($3^{rd}$ 1989), Progress in Clinical and Biological Research 343.

While this technique is advantageously applied to circulating cells in the blood, it may also be applied to cells in culture or to cells from solid tissues which have been suspended The alterations possible allow cellular "reprogramming", through external engineered additions to the cell structure. It is also conceivable to remove portions of the treated cells, such as membrane components having relatively lower transition temperatures. These cell changes may be temporary, for example the addition of exogenous receptors to cells. Thus, repeated treatments may be required to maintain a high level effect. The treatment may employ a plasmapheresis device or involve removal, treatment and reinfusion of cells into a patient.

Figure 18:
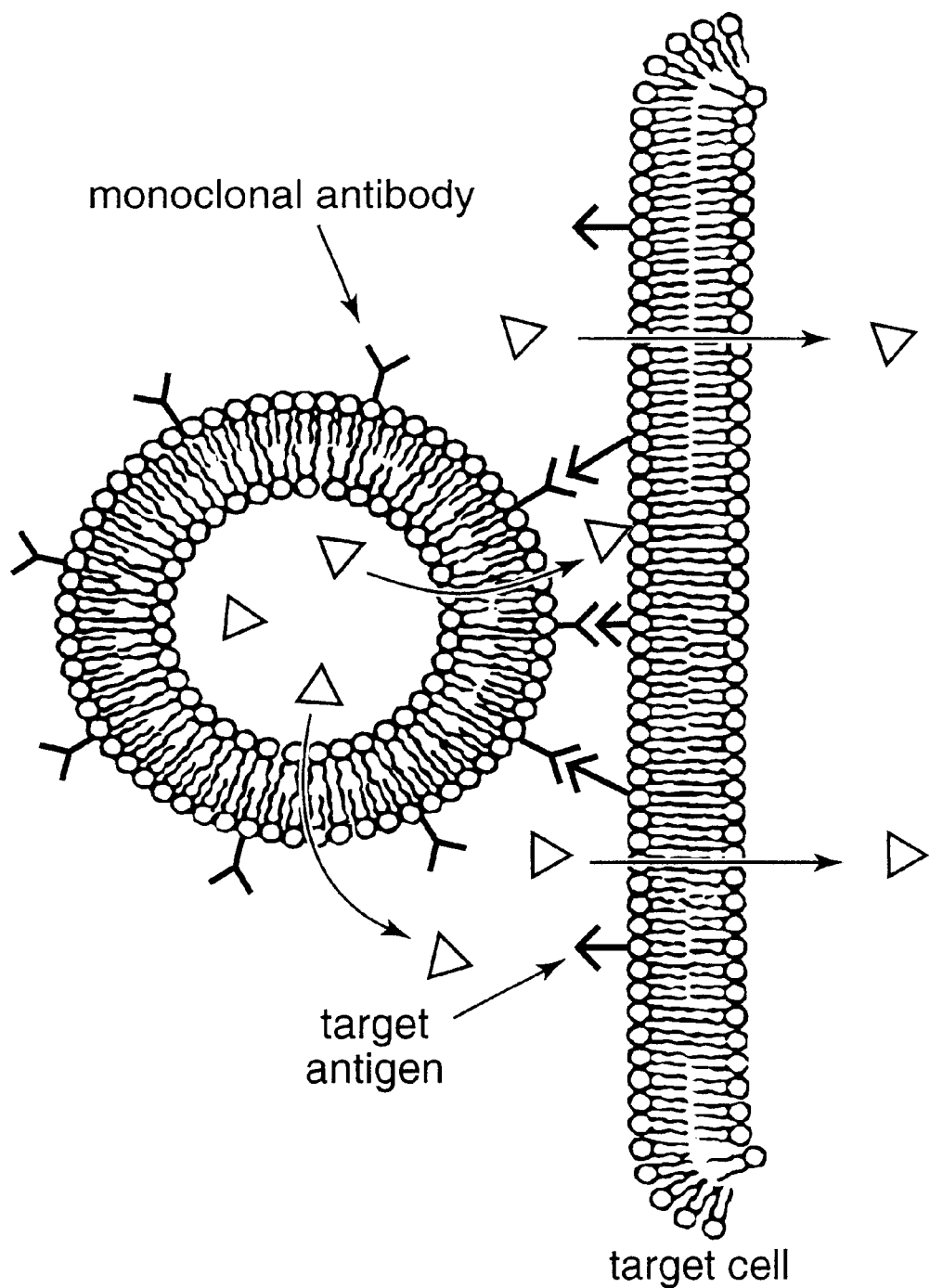
FIG. 18 shows the interaction of antibodies on the surface of a liposome with complementary cell surface structures.

In some cases, the cells are or are made differentially sensitive to the RTCP treatment. In other cases, during treatment, a selective effect is applied to a population of cells which are otherwise of equivalent sensitivity to RTCP treatment. For example, vesicles or liposomes having receptors or monoclonal antibodies are mixed with unsorted cells and the mixture subjected to RTCP. The receptors or monoclonal antibodies interact selectively with certain cells, having complementary cell surface structures. This is shown schematically in FIG. 18, in which the "Y" structures are specific antibodies against the arrow structures on the cell surface, and the triangular structures represent a specific treatment, which readily diffuses out of a liposome, being provided to the cell. RTCP technology allows fusion of the liposome membrane with the cellular membrane, so that the treatment is injected directly into the cell.

The RTCP process raises the cell membranes to a temperature at which they begin to become unstable. The close proximity of the vesicles or liposomes with some cells causes a membrane fusion, which may be a physical effect or a cell mediated effect. The liposome contains either within its core or on its surface a desired treatment for the cell. This treatment may be, for example, lethal to the selected population, for example a cytotoxin, or membrane lytic agent, such as alpha cyclodextrin or certain cyclic peptides, a free radical promoter or inhibitor (See, Proc. Int. Symp. on Free radicals in Diagnostic Medicine: A Systems Approach to Laboratory Technology, Clinical Correlations and Antioxidant Therapy (1993)), or a more benign treatment, such as a desired cell surface receptor system, antibiotic agent, or the like. See, Fauvelle, F. et al., "Mechanism of a-Cyclodextrin-Induced Hemolysis. 1. The Two-Step Extraction of Phosphoinositol from the Membrane", J. Pharm. Sciences, 86(8):935–943 (1997). The advantage of this scheme is that selectivity may be increased, while liposome technology employed to target cells which do not normally take up liposomes.

EXAMPLE 18

Immunological and Vaccine Effects

The RTCP technique has the ability to expose normally hidden antigens from prokaryotic and eukaryotic cells, and likely from membrane-bound viruses, to the extracellular media. Thus, the technique may find application in the production of vaccines or autovaccination of individuals through the processing of plasma in a plasmapheresis apparatus.

While RTCP holds this promise, the technique of simple exposure of antigens is the oldest of killed vaccine techniques, and in many cases is inferior to more advanced techniques. However, where the causative agent is unknown or occult, this technique may allow rapid treatment with relatively safe conditions. In addition, this technique may also be able to address rapidly mutating species, such as HIV variants and cancer cells, by exposing the actual antigens present, rather those of an exemplar.

While raw disrupted cellular material has been used in the past as the basis to establish an immune response, this is considered inferior to a vaccine engineered to develop a specific immune response to an identified component of the cell, to which an immune response results in useful activation of the body's immune system.

It should be understood that the preferred embodiments and examples described herein are for illustrative purposes only and are not to be construed as limiting the scope of the present invention, which is properly delineated only in the appended claims.

What is claimed is:

1. In a method for treating a cell associated with heat-labile macromolecules, to at least temporarily alter a lipid membrane of cell, comprising rapidly heating, under steady state conditions, the cell at a rate sufficient to produce an instability in the lipid membrane without substantially denaturing the heat-labile macromolecules, the improvement comprising producing a persistent non-lethal change in the cell.

2. The method according to 1, wherein the cell is a prokaryotic cell.

3. The method according to claim 1, wherein the cell is a eukaryotic cell.

4. The method according to claim 1, wherein the persistent non-lethal change comprises a fusion of the cell with another lipid membrane-containing structure.

5. The method according to claim 1, wherein the change comprises a release of compounds from the cell.

6. The method according to claim 1, wherein the change comprises an uptake of compounds into the cell.

7. The method according to claim 1, wherein the instability results when at least a portion of the lipid membrane changes from a bilayer state to a non-bilayer state.

8. The method according to claim 1, wherein said heating causes a non-linear change in packing density of molecules forming the lipid membrane.

9. The method according to claim 1, wherein the cell comprises a formed blood component.

10. The method according to claim 1, wherein the instability exposes normally hidden antigens of the cell.

11. The method according to claim 1, wherein said heating is effected by condensation of steam.

12. The method according to claim 1, wherein the cell is suspended in a medium, wherein the medium is atomized prior to heating and heated through exposure to steam.

13. The method according to claim 1, wherein the cell is subject to mechanical forces synchronized with and independent of said heating.

14. The method according to clam 1, further comprising the step of maintaining operation in a steady state condition for an extended period of time for the sequential treatment of a plurality of cells.

15. In a method for treating a cellular lipid membrane to alter the cellular lipid membrane, comprising rapidly heating one or some cells at a sufficient rate to produce an instability in the cellular lipid membrane, the improvement comprising heating under such conditions as to avoid lysing the cellular lipid membrane, while producing a persistent, non-lethal change in the cells.

16. The method according to claim 15, wherein the persistent changes comprises a membrane fusion.

17. The method according to claim 15, wherein the structure is heated at a rate sufficient and through a range appropriate to cause an abrupt glass transition in a portion of the membrane of the cellular lipid-membrane containing structure.

18. The method according to claim 15, wherein a molecular lipid bilayer structure of the membrane is altered by said heating.

19. The method according to claim 15, wherein the heating is effected by condensation of steam in proximity to the structure.

20. The method according to claim 15, further comprising the step of maintaining operation in a steady state condition for an extended period of time for the sequential treatment of a plural of cells.

* * * * *